(12) United States Patent
Lee et al.

(10) Patent No.: US 11,939,580 B2
(45) Date of Patent: Mar. 26, 2024

(54) CONSTRUCT OF SELF-CIRCULARIZATION RNA

(71) Applicant: Rznomics Inc., Yongin-si (KR)

(72) Inventors: Seong-Wook Lee, Seoul (KR); Kyung Hyun Lee, Seongnam-si (KR); Seung Ryul Han, Yongin-si (KR); Ji Hyun Kim, Seoul (KR); Seongcheol Kim, Seongnam-si (KR)

(73) Assignee: Rznomics Inc., Yongin-si (KR)

( * ) Notice: Subject to any disclaimer, the term of this patent is extended or adjusted under 35 U.S.C. 154(b) by 0 days.

(21) Appl. No.: 18/045,860

(22) Filed: Oct. 12, 2022

(65) Prior Publication Data
US 2023/0212574 A1 Jul. 6, 2023

Related U.S. Application Data

(63) Continuation-in-part of application No. PCT/KR2022/003377, filed on Mar. 10, 2022.

(30) Foreign Application Priority Data

Mar. 10, 2021 (KR) .......... 10-2021-0031225
Mar. 10, 2022 (KR) .......... 10-2022-0029918

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/124* (2013.01); *C12N 2310/532* (2013.01)

(58) Field of Classification Search
None
See application file for complete search history.

(56) References Cited

U.S. PATENT DOCUMENTS

| | | | |
|---|---|---|---|
| 5,712,128 A | 1/1998 | Been et al. | |
| 6,210,931 B1 | 4/2001 | Feldstein et al. | |
| 2010/0137407 A1 | 6/2010 | Abe et al. | |
| 2010/0305197 A1 | 12/2010 | Che | |

FOREIGN PATENT DOCUMENTS

| | | |
|---|---|---|
| EP | 3 920 976 A2 | 12/2021 |
| KR | 10-0235792 B1 | 12/1999 |
| WO | 2018/237372 A1 | 12/2018 |
| WO | 2019/236673 A1 | 12/2019 |
| WO | 2020/237227 A1 | 11/2020 |
| WO | 2021/113777 A2 | 6/2021 |
| WO | 2021/155171 A1 | 8/2021 |
| WO | 2021/155175 A1 | 8/2021 |
| WO | 2021/189059 A2 | 9/2021 |
| WO | 2021/226597 A2 | 11/2021 |
| WO | 2021/236855 A1 | 11/2021 |

OTHER PUBLICATIONS

Thomas B. Campbell et al., "Mutations in the Telrahymena Ribozyme Internal Guide Sequence: Effects on Docking of the PI Helix into the Catalytic Core and Correlation with Catalytic Activity", Biochemistry, 1996, pp. 11493-11502, vol. 35.
R. Alexander Wesselhoeft et al., "Engineering circular RNA for potent and stable translation in eukaryotic cells", Nature Communications, 2018, pp. 1-10, vol. 9, No. 2629.
International Search Report for PCT/KR2022/003377 dated Jun. 13, 2022 (PCT/ISA/210).

*Primary Examiner* — Kimberly Chong
(74) *Attorney, Agent, or Firm* — Sughrue Mion, PLLC

(57) ABSTRACT

A self-circularization RNA construct that can be expressed in a DNA vector and simultaneously circularized through a self-targeting and splicing reaction to form a circRNA is disclosed. The circRNA can consist only of a gene of interest which can be a coding, non-coding, or a combination thereof. The gene of interest has the advantage of being able to rapidly express a peptide or protein. The formed circRNA has a circular structure and has a stable and high half-life because 5' and 3' ends are not exposed. Accordingly, functional RNA such as miRNA, anti-miRNA, siRNA, shRNA, aptamer, functional RNA for gene/RNA editing, ADAR (adenosine deaminase acting on the RNA)-recruiting RNA, mRNA vaccine, mRNA therapeutic agent, vaccine adjuvant, and CAR-T mRNA can be produced as a stable circRNA in cells.

27 Claims, 32 Drawing Sheets
Specification includes a Sequence Listing.

FIG. 2D

T7 Promoter                                                                 Antisense 150
GGGATTCGAACATCGATTAATACGACTCACTATAGGGGCATGATGATTGAATTGTGACGAATTCGGCGGCCAGCAGGAACTGCCATGGAGTCAGCCAGGTAGTactgtggtactgaagTg gctggtaccacccgttcgattggagaagggcacgttaggggccttcgttgtgcattatggctgactgaccgAATTCcgtactgcGccaaaAAAGTTATCAGGCATGCACCTGGTAGTAGTCT
                                                                P1-P10 IGS

TTAAACCAATAGATTCGATCGGTTAAAAGCCAAGACCGTTAAATTCGCGGAAAGGGGTCAACAGCCGTTCAGTACCAAGTCTCAGGGGAAATTTGAGATGCCTTGCAAAGGGTATG
                                            Trans-Splicing Ribozyme

GTAATAAGCTGACGGACATGCTGTCCTAACCACGCAGCCAAGTCCAAGATCTTCGTGATATGGATGATGATCACAGACTAAGTGTCGGTCGGGAAGATGTATTCTCTCAT

AAGGATATAGTCGGACCTCTCCTTAATGGGAGCTAGCGGATGAAGTGATGCAACACTGGGAGCCGTCGGGGAACTAATTTGTATGCGAAAGTATATTGATTAGTTTGGAGTACTCGcgagtacg CTTAAGAAAAAAAGagggcccgaaaacctgccctgtcttcttgacgacattcctaggotgtcttgaatgtctgttgaatgcaatcgaaaccaggtcctctgaagctttcctctgaagtcctgaaacaa
                                                                EMCV IRES cgtctgtagctagaccttgaaggaaccttgaaggggggaaccacctggcgatagggtgcctctgccgcaggtgcctctgccgcaggtgcctaccggcacaaaaggccgacaaaccgcgaaaggcggcacaaccccgaaagtgtgattgatagttgtgaaggcgtaaatgg ctctccttaagcgtattcaacaatgataaGcttgcacaaaccCTTAAGaccggtAtgggaaaagtttattccctctgcaatctgcactcgaaatgcaagcagccaaccaagaagcatcctcagacctctcgtgcccagcaacttcg ctttgaaaaacctgataaGcttgcacaaaccCTTAAGaccggtAtgggaaaagtttattccctctgcaatctgcactgaaatgcaagcagccaaccaagaagcatcctcaaatcatgtgtccacaatgtaggtccaatcaagtgcaccccaagat
                                            Gene of interest (GOI, Gaussia Luciferase)

cgaccacggattcgattctaaccgagaacgacctacccaagcggtcgtcaagcatcctgccgtacgggcatgagacgactgtagaccaaggcaggatgcaagatcaaggggcgcgtgtgactaaAA gtatgactgcacaactgctgctccaagaacctaccaagggcttgccactgcaatgttcaacctgctccaagacctgctccaagagccctaacttctacgtgcctctccaatgaggacccActtcgagtaccacagtACTAC
                                                                Antisense Binding Sequence

CTGGCTGAGCCAGTTCTCCAAGCCCGCCCCAAGTTGCCTCGAGCAGGCGCTGCTCGAGAGATCT (SEQ ID NO: 10)

Target Site
AAAAAAAaccggt77GGGTGSGagcagcacggttagcagcacgagagcgccttaacttctacgtgccttctcccattcacgcacgcccttctcaattgcacgtacgggtcgctctgcgcctgaccActtcgagtaccacagtACTAC

FIG. 7A

Assay Conditions

- ✓ HPLC system: Agilent 1290 Infinity II Bio UHPLC
- ✓ Analytical column: Agilent PLRP-S 4000A 8um, 2.1 x 50mm
- ✓ Injection volume: 2 μL (Prep 10 – 20uL)
- ✓ Flow rate: 0.5 mL/min
- ✓ Column oven temperature: 60 °C
- ✓ Detector: UV 260nm
- ✓ Mobile phase A: 100mM Hexylamine acetate pH7.0
- ✓ Mobile phase B: 100mM Hexylamine acetate in acetonitrile
- ✓ Gradient

- Fraction collection

| Time(min) | %A | %B |
|---|---|---|
| 0 | 70 | 30 |
| 2 | 70 | 30 |
| 15 | 45 | 55 |
| 16 | 10 | 90 |
| 17 | 10 | 90 |
| 17.1 | 70 | 30 |
| 20 | 70 | 30 |

- Analytical

| Time(min) | %A | %B |
|---|---|---|
| 0 | 80 | 20 |
| 2 | 80 | 20 |
| 50 | 40 | 60 |
| 51 | 10 | 90 |
| 53 | 10 | 90 |
| 53.1 | 80 | 20 |
| 56 | 80 | 20 |

Fraction collection was conducted at timing ranging from 9 min to 12 min at 0.1min interval with 2 position/6 port valve position increases, and the fractions were collected at 96 wellplate (PP, 250 uL).

FIG. 14

T7 Promoter *IGS*

GGGATTCGAACATCGATTAATACGACTCACTATAGGGccccaaAAAAGTTATCAGGCATGCACCTGGTAGCTAGTCTTAAACCAATAGATTGCATCGGTTTAAAAGGCAAGACCGTCAAA TTGCGGGAAAGGGGTCAACAGCCGTTCAGTACCAAGTCTCAGGGGAAACTTTGAGATGGCCTTGCAAAGGGTAGTAATAAGCTGACGGACATGGTCTAACCACGCAGCCAAGTCCT

Trans-Splicing Ribozyme

AAGTCAACAGATCTTCTGTTGATATGGATGCAGTTCACAGAGACTAAATGTCGGTCGGGGAAGATGTATTCTTCATAAGATATAGTCGGACCTCTCCTTAATGGGAGCTAGCGGGATGAAGT

GATGCAACACTGGAGCCGCTGGGAACTAATAATTTGTATGCGAACTACTCGccgagtacgCTTAAGAAAAAGaggcccgaaacctgccctgtctttgacgag cattccctaggggtttccccctgccaaagaatgaatgcaagttgtttaatgtgttgatgggaagcagagttctcttgaagcacgcgaccttgaagcactgccgaaacgtgctct gcggccaaagccacgtgatataagaccaatgccaacacccaatgcaaatgcccaaatgccaacacaagttgcgtatgattcaacaggacagcatgaaggcgaacagtcccaattgta

EMCV IRES tggagctgatctgagtcgagcctccagtgcacatgcttagtcacatgtgttagtcctaggccccgaaccacgggaacgtgtttccttgaaacatcacgatgatcacgatctcatggagtc aaagttttcgtttgcctgatcgacatcgtgtgccgagccgaaagccccgaaagttcaacacatgtgccgacaactcgctgaccggatccgatccgatccgggaagttgccggcaagagctgccgctg

Gene of interest (GOI, Gaussia Luciferase)

gaggttgctcaaagacagagctgagggaagccaatgctgagctgcaacctggaaatgcccgaagagtgattcgatctgccgtccaatcaagtcgaagagagtgcaagtcccaatcgcccacctaccgagccatgccgacctgccaaacctaccgaggacaaagagtccgcac aggacggcatgaggcatgaggcgaatcgatcgaatcgatcgacattccagatccctggttcaagctaggcgagcccatggagcctgcaacgagtcatgcccagggatcctgtgtgtggagctgccacaactgactcgtgtgacttcaccaaggggttgccactgccagtgttccgacct

Target Site gctcaagaagttgctgctccgcaacgcctgtcgaactttgccagcaagattcagggtgacattcagtgacattgacaacccgggccgttgtgacctaaAAAAAAAAccgaggtt77GGGT (SEQ ID NO: 29)

M: GenRuler 50 bp DNA Ladder (Thermo Scientific, SM0373)
1: AU-rich-EMCV-IRES-Gluci (P1, No AS) IVT RNA + RNase R (RT-PCR)
2: 2 sites-EMCV-IRES-Gluci (P1, No AS) IVT RNA + RNase R (RT-PCR: Target Site 1)
3: 2 sites-EMCV-IRES-Gluci (P1, No AS) IVT RNA + RNase R (RT-PCR: Target Site 2)
4: No complementary-EMCV-IRES-Gluci (P1, No AS) IVT RNA + RNase R (RT-PCR)

```
SEQUENCE LISTING

Sequence total quantity: 48
SEQ ID NO: 1            moltype =    length =
SEQUENCE: 1
000

SEQ ID NO: 2            moltype =    length =
SEQUENCE: 2
000

SEQ ID NO: 3            moltype = DNA  length = 20
FEATURE                 Location/Qualifiers
misc_feature            1..20
                        note = T7 promoter
source                  1..20
                        mol_type = other DNA
                        organism = synthetic construct
SEQUENCE: 3
taatacgact cactataggg                                             20

SEQ ID NO: 4            moltype = DNA  length = 151
FEATURE                 Location/Qualifiers
misc_feature            1..151
                        note = AS 150: AS region of expression vector for
                         self-circularizationRNA
source                  1..151
                        mol_type = other DNA
                        organism = synthetic construct
SEQUENCE: 4
cggcggccag catggagaac tgccatggct cagccaggta gtactgtggg tactcgaagt  60
ggctgcgtac cacaccgtc  gcattggaga agggcacgta gaagttaggg ccttctgtgc  120
cattcatggc tgtggccctt gtggctgacc c                                151

SEQ ID NO: 5            moltype =    length =
SEQUENCE: 5
000

SEQ ID NO: 6            moltype = DNA  length = 387
FEATURE                 Location/Qualifiers
misc_feature            1..387
                        note = ribozyme region of expression vector for
                         self-circularization RNA
source                  1..387
                        mol_type = other DNA
                        organism = synthetic construct
SEQUENCE: 6
aaaagttatc aggcatgcac ctggtagcta gtctttaaac caatagattg catcggttta  60
aaaggcaaga ccgtcaaatt gcgggaaagg ggtcaacagc cgttcagtac caagtctcag  120
gggaaacttt gagatggcct tgcaaagggt atggtaataa gctgacggac atggtcctaa  180
ccacgcagcc aagtcctaag tcaacagatc ttctgttgat atggatgcag ttcacagact  240
aaatgtcggt cggggaagat gtattcttct cataagatat agtcggacct ctccttaatg  300
ggagctagcg gatgaagtga tgcaacactg gagccgctgg gaactaattt gtatgcgaaa  360
gtatattgat tagttttgga gtactcg                                     387

SEQ ID NO: 7            moltype = DNA  length = 463
FEATURE                 Location/Qualifiers
misc_feature            1..463
                        note = EMCV IRES region of expression vector for
                         self-circularizationRNA
source                  1..463
                        mol_type = other DNA
                        organism = synthetic construct
SEQUENCE: 7
gagggcccgg aaacctggcc ctgtcttctt gacgagcatt cctagggggtc tttcccctct  60
cgccaaagga atgcaaggtc tgttgaatgt cgtgaaggaa gcagttcctc tggaagcttc  120
ttgaagacaa acaacgtctg tagcgaccct ttgcaggcag cggaaccccc cacctggcga  180
caggtgcctc tgcggccaaa agccacgtgt ataagataca cctgcaaagg cggcacaacc  240
```

```
ccagtgccac gttgtgagtt ggatagttgt ggaaagagtc aaatggctct cctcaagcgt   300
attcaacaag gggctgaagg atgcccagaa ggtaccccat tgtatgggat ctgatctggg   360
gcctcggtgc acatgcttta catgtgttta gtcgaggtta aaaaaacgtc taggcccccc   420
gaaccacggg gacgtggttt tcctttgaaa aacacgatga taa                    463
```

| | | |
|---|---|---|
| SEQ ID NO: 8 | moltype = DNA  length = 558 | |
| FEATURE | Location/Qualifiers | |
| misc_feature | 1..558 note = transgene region of expression vector for self-circularizationRNA: Gaussia Luciferase | |
| source | 1..558 mol_type = other DNA organism = synthetic construct | |

SEQUENCE: 8
```
atgggagtca aagttctgtt tgccctgatc tgcatcgctg tggccgaggc caagcccacc    60
gagaacaacg aagacttcaa catcgtggcc gtggccagca acttcgcgac cacggatctc   120
gatgctgacc gcgggaagtt gcccggcaag aagctgccgc tggaggtgct caaagagatg   180
gaagccaatg cccggaaagc tggctgcacc aggggctgtc tgatctgcct gtcccacatc   240
aagtgcacgc ccaagatgaa gaagttcatc ccaggacgtc gccacaccta cgaaggcgac   300
aaagagtccg cacagggcgg cataggcgag gcgatcgtcg acattcctga gattcctggg   360
ttcaaggact tggagcccat ggagcagttc atcgcacagg tcgatctgtg tgtggactgc   420
acaactggct gcctcaaagg gctttgccaac gtgcagtgtt ctgacctgct caagaagtgg   480
ctgccgcaac gctgtgcgac ctttgccagc aagatccagg ccaggtggaa caagatcaag   540
ggggccggtg gtgactaa                                                 558
```

| | | |
|---|---|---|
| SEQ ID NO: 9 | moltype = DNA  length = 150 | |
| FEATURE | Location/Qualifiers | |
| misc_feature | 1..150 note = ABS region of expression vector for self-circularization RNA | |
| source | 1..150 mol_type = other DNA organism = synthetic construct | |

SEQUENCE: 9
```
gggtcagcca aagggccac agccatgaat ggcacagaag ccctaacttc tacgtgccc     60
ttctccaatg cgacgggtgt ggtacgcagc cacttcgagt acccacagta ctacctggct   120
gagccatggc agttctccat gctggccgcc                                   150
```

| | | |
|---|---|---|
| SEQ ID NO: 10 | moltype = DNA  length = 1908 | |
| FEATURE | Location/Qualifiers | |
| misc_feature | 1..1908 note = DNA template encoding self-circularization RNA of Example 1 | |
| source | 1..1908 mol_type = other DNA organism = synthetic construct | |

SEQUENCE: 10
```
gggattcgaa catcgattaa tacgactcac tatagggca tcgattgaat tgtcgacgaa    60
tcggcggcc agcatggaga actgccatgg ctcagccagg tagtactgtg ggtactcgaa   120
gtggctgcgt accacacccg tcgcattgga agggcacg tagaagttag ggccttctgt   180
gccattcatg gctgtggccc ttgtggctga cccgaattcc gtactccgcc caaaaaagtt   240
atcaggcatg cacctggtag ctagtctttta aaccaataga ttgcatcggt ttaaaaggca   300
agaccgtcaa attgcgggaa aggggtcaac agccgttcag taccaagtct caggggaaac   360
tttgagatgg ccttgcaaag ggtatggtaa taagctgacg gacatggtcc taaccacgca   420
gccaagtcct aagtcaacag atcttctgtt gatatggatg cagttcacag actaaatgtc   480
ggtcggggaa gatgtattct ctctcataaga tatagtcgga cctctcctta atggagcta   540
gcggatgaag tgatgcaaca ctggagccgc tgggaactaa tttgtatgcg aaagtatatt   600
gattagtttt ggagtactcg cgagtacgct taagaaaaaa aaagaggc ccggaaacct   660
ggccctgtct tcttgacgag cattcctagg ggtctttccc ctctcgcaa aggaatgcaa   720
ggtctgttga atgtcgtgaa ggaagcagtt cctctggaag cttcttgaag acaaacaacg   780
tctgtagcga ccctttgcag gcagcggaac ccccacctg cgacaggtg cctctgcggc   840
caaaagccac gtgtataaga tacacctgca aggcggcac aacccagtg ccacgttgtg   900
agttggatag ttgtggaaag agtcaaatgg ctctcctcaa gcgtattcaa caagggctg   960
aaggatgccc agaaggtacc ccattgtatg ggatctgatc tgggcctcg gtgcacatgc  1020
tttacatgtg tttagtcgag gttaaaaaaa cgtctaggcc cccgaacca ggggacgtg  1080
gttttcctttt gaaaaacacg atgataagct tgccacaacc cttaagaccg gtatgggagt  1140
caaagttctg tttgccctga tctgcatcgc tgtggccgag gccaagccca ccgagaacaa  1200
cgaagacttc aacatcgtgg ccgtggccag caacttcgcg accacggatc tcgatgctga  1260
ccgcgggaag ttgcccggca aagctgcc ctggaggtgc tcaaagaga tggaagcag  1320
tgccccgaaa gctggctgca ccaggggctg tctgatctgc ctgtcccaca tcaagtgcac  1380
gcccaagatg aagaagttca tcccaggacg ctgccacacc tacgaaggcg acaaagagtc  1440
cgcacagggc ggcataggcg aggcgatcgt cgacattcct gagattcctg ggttcaagga  1500
cttggagccc atggagcagt tcatcgcaca ggtcgatctg tgtgtggact gcacaactgg  1560
ctgcctcaaa gggctttgcc aacgtgcagt tctgacctgc tcaagaagt ggctgccgca  1620
acgctgtgcg acctttgcca gcaagatcca gccaggtg acaagatca ggggccgtg  1680
tgtgactaa aaaaaaaaaa accgtttggt gtgggagcag ccacgggtca gccacaaggg  1740
ccacagccat gaatgcaca gaaggcccta acttctacgt gcccttctcc aatgcgacgg  1800
gtgtggtacg cagccacttc gagtacccac agtactacct ggctgagcca tggcagttct  1860
ccatgctggc cgccaagctt gcctcgagca gcgctgctca agagatct               1908
```

```
SEQ ID NO: 11              moltype = DNA  length = 56
FEATURE                    Location/Qualifiers
misc_feature               1..56
                           note = T7 Circular Forward primer
source                     1..56
                           mol_type = other DNA
                           organism = synthetic construct
SEQUENCE: 11
gggattcgaa catcgattaa tacgactcac tatagggca tcgattgaat tgtcga          56

SEQ ID NO: 12              moltype = DNA  length = 34
FEATURE                    Location/Qualifiers
misc_feature               1..34
                           note = T7 Circular Reverse primer
source                     1..34
                           mol_type = other DNA
                           organism = synthetic construct
SEQUENCE: 12
agatctctcg agcagcgctg ctcgaggcaa gctt                                  34

SEQ ID NO: 13              moltype = DNA  length = 21
FEATURE                    Location/Qualifiers
misc_feature               1..21
                           note = Circular STS Forward primer of the example 2-2
source                     1..21
                           mol_type = other DNA
                           organism = synthetic construct
SEQUENCE: 13
ccctgagtgg ctgagctcag g                                                21

SEQ ID NO: 14              moltype = DNA  length = 23
FEATURE                    Location/Qualifiers
misc_feature               1..23
                           note = Circular STS Reverse primer of the example 2-2
source                     1..23
                           mol_type = other DNA
                           organism = synthetic construct
SEQUENCE: 14
cagcaagcat actaaattgc cag                                              23

SEQ ID NO: 15              moltype = DNA  length = 25
FEATURE                    Location/Qualifiers
misc_feature               1..25
                           note = Circular STS Forward primer of the example 3
source                     1..25
                           mol_type = other DNA
                           organism = synthetic construct
SEQUENCE: 15
caaggacttg gagcccatgg agcag                                            25

SEQ ID NO: 16              moltype = DNA  length = 23
FEATURE                    Location/Qualifiers
misc_feature               1..23
                           note = Circular STS Reverse primer 2 of the example 3
source                     1..23
                           mol_type = other DNA
                           organism = synthetic construct
SEQUENCE: 16
tgtgccgcct ttgcaggtgt atc                                              23

SEQ ID NO: 17              moltype = DNA  length = 50
FEATURE                    Location/Qualifiers
misc_feature               1..50
                           note = DNA sequence for AS50 region
source                     1..50
                           mol_type = other DNA
                           organism = synthetic construct
SEQUENCE: 17
aagttagggc cttctgtgcc attcatggct gtggcccttg tggctgaccc                 50

SEQ ID NO: 18              moltype = DNA  length = 100
FEATURE                    Location/Qualifiers
misc_feature               1..100
                           note = DNA sequence for AS100 region
source                     1..100
                           mol_type = other DNA
                           organism = synthetic construct
SEQUENCE: 18
```

```
actcgaagtg gctgcgtacc acacccgtcg cattggagaa gggcacgtag aagttagggc    60
cttctgtgcc attcatggct gtggcccttg tggctgaccc                          100

SEQ ID NO: 19          moltype = DNA   length = 150
FEATURE                Location/Qualifiers
misc_feature           1..150
                       note = DNA sequence for AS150 region
source                 1..150
                       mol_type = other DNA
                       organism = synthetic construct
SEQUENCE: 19
ggcggccagc atggagaact gccatggctc agccaggtag tactgtgggt actcgaagtg    60
gctgcgtacc acacccgtcg cattggagaa gggcacgtag aagttagggc cttctgtgcc   120
attcatggct gtggcccttg tggctgaccc                                    150

SEQ ID NO: 20          moltype = DNA   length = 200
FEATURE                Location/Qualifiers
misc_feature           1..200
                       note = DNA sequence for AS200 region
source                 1..200
                       mol_type = other DNA
                       organism = synthetic construct
SEQUENCE: 20
agcgtgagga agttgatggg gaagcccagc acgatcagca gaaacatgta ggcggccagc    60
atggagaact gccatggctc agccaggtag tactgtgggt actcgaagtg gctgcgtacc   120
acacccgtcg cattggagaa gggcacgtag aagttagggc cttctgtgcc attcatggct   180
gtggcccttg tggctgaccc                                               200

SEQ ID NO: 21          moltype = DNA   length = 250
FEATURE                Location/Qualifiers
misc_feature           1..250
                       note = DNA sequence for AS250 region
source                 1..250
                       mol_type = other DNA
                       organism = synthetic construct
SEQUENCE: 21
ggatgtagtt gagaggcgtg cgcagcttct tgtgctggac ggtgacgtag agcgtgagga    60
agttgatggg gaagcccagc acgatcagca gaaacatgta ggcggccagc atggagaact   120
gccatggctc agccaggtag tactgtgggt actcgaagtg gctgcgtacc acacccgtcg   180
cattggagaa gggcacgtag aagttagggc cttctgtgcc attcatggct gtggcccttg   240
tggctgaccc                                                          250

SEQ ID NO: 22          moltype = DNA   length = 300
FEATURE                Location/Qualifiers
misc_feature           1..300
                       note = DNA sequence for AS300 region
source                 1..300
                       mol_type = other DNA
                       organism = synthetic construct
SEQUENCE: 22
ggtgaagcca cctaggacca tgaagaggtc agccacggct aggttgagca ggatgtagtt    60
gagaggcgtg cgcagcttct tgtgctggac ggtgacgtag agcgtgagga agttgatggg   120
gaagcccagc acgatcagca gaaacatgta ggcggccagc atggagaact gccatggctc   180
agccaggtag tactgtgggt actcgaagtg gctgcgtacc acacccgtcg cattggagaa   240
gggcacgtag aagttagggc cttctgtgcc attcatggct gtggcccttg tggctgaccc   300

SEQ ID NO: 23          moltype = DNA   length = 10
FEATURE                Location/Qualifiers
misc_feature           1..10
                       note = DNA sequence for A10: spacer region
source                 1..10
                       mol_type = other DNA
                       organism = synthetic construct
SEQUENCE: 23
aaaaaaaaaa                                                           10

SEQ ID NO: 24          moltype = DNA   length = 30
FEATURE                Location/Qualifiers
misc_feature           1..30
                       note = DNA sequence for A30: spacer region
source                 1..30
                       mol_type = other DNA
                       organism = synthetic construct
SEQUENCE: 24
aaaaaaaaaa aaaaaaaaaa aaaaaaaaaa                                     30

SEQ ID NO: 25          moltype = DNA   length = 50
FEATURE                Location/Qualifiers
misc_feature           1..50
```

```
                        note = DNA sequence for A50: spacer region
source                  1..50
                        mol_type = other DNA
                        organism = synthetic construct
SEQUENCE: 25
aaaaaaaaaa aaaaaaaaaa aaaaaaaaaa aaaaaaaaaa aaaaaaaaaa                  50

SEQ ID NO: 26           moltype = DNA  length = 35
FEATURE                 Location/Qualifiers
misc_feature            1..35
                        note = DNA sequence for control 1: spacer region
source                  1..35
                        mol_type = other DNA
                        organism = synthetic construct
SEQUENCE: 26
ggtagtggtg ctactaactt cagcctgctg aagca                                  35

SEQ ID NO: 27           moltype = DNA  length = 34
FEATURE                 Location/Qualifiers
misc_feature            1..34
                        note = DNA sequence for control 2: spacer region
source                  1..34
                        mol_type = other DNA
                        organism = synthetic construct
SEQUENCE: 27
ggtagtaaac tactaactac aacctgctga agca                                   34

SEQ ID NO: 28           moltype =     length =
SEQUENCE: 28
000

SEQ ID NO: 29           moltype = DNA  length = 1522
FEATURE                 Location/Qualifiers
misc_feature            1..1522
                        note = DNA template encoding self-circularization RNA of
                         Example 7
source                  1..1522
                        mol_type = other DNA
                        organism = synthetic construct
SEQUENCE: 29
gggattcgaa catcgattaa tacgactcac tatagggggcc caaaaaagtt atcaggcatg      60
cacctggtag ctagtctta aaccaataga ttgcatcggt ttaaaaggca agaccgtcaa       120
attgcgggaa aggggtcaac agccgttcag taccaagtct caggggaaac tttgagatgg      180
ccttgcaaag ggtatggtaa taagctgacg gacatggtcc taaccacgca gccaagtcct      240
aagtcaacag atcttctgtt gatatggatg cagttcacag actaaatgtc ggtcggggaa      300
gatgtattct tctcataaga tatagtcgga cctctcctta atgggagcta gcggatgaag      360
tgatgcaaca ctggagccgc tgggaactaa tttgtatgcg aaagtatatt gattagtttt      420
ggagtactcg cgagtacgct taagaaaaaa aaaagagggc ccggaaacct ggccctgtct      480
tcttgacgag cattcctagg ggtctttccc ctctcgccaa aggaatgcaa ggtctgttga      540
atgtcgtgaa ggaagcagtt cctctggaag cttcttgaag acaaacaacg tctgtagcga      600
cccttttgcag gcagcggaac cccccacctg gcgacaggtg cctctgcggc caaaagccac      660
gtgtataaga tacacctgca aaggcggcac aaccccagtg ccacgttgtg agttggatag      720
ttgtggaaag agtcaaatgg ctcctcctcaa gcgtattcaa caaggggctg aaggatgccc     780
agaaggtacc ccattgtatg ggatctgatc tggggcctcg gtgcacatgc tttacatgtg      840
tttagtcgag gttaaaaaaa cgtctaggcc ccccgaacca cggggacgtg gttttccttt      900
gaaaaacacg atgataagct tgccacaacc cttaagaccg gtatgggagt caaagttctg      960
tttgccctga tctgcatcgc tgtggccgag gccaagccca ccgagaacaa cgaagacttc     1020
aacatcgtgg ccgtggccag caacttcgcg accacggatc tcgatgctga ccgcgggaag     1080
ttgccggca agaagctgcc gctggaggtg ctcaaagaga tggaagccaa tgccggaaa       1140
gctggctgca ccaggggctg tctgatctgc ctgtcccaca tcaagtgcac gccaagatg       1200
aagaagttca tcccaggacg ctgccacacc tacgaaggcg acaaagagtc cgcacagggc     1260
ggcataggca aggcgatcgt cgacattcct gagattcctg ggttcaagga cttgagccc      1320
atggagcagt tcatcgcaca ggtcgatctg tgtgtggact gcacaactgg ctgcctcaaa     1380
gggcttgcca acgtgcagtg ttctgacctg ctcaagaagt ggctgccgca acgctgtgcg     1440
acctttgcca gcaagatcca gggccaggtg gacaagatca aggggggccgg tggtgactaa    1500
aaaaaaaaaa accggtttgg gt                                               1522

SEQ ID NO: 30           moltype =     length =
SEQUENCE: 30
000

SEQ ID NO: 31           moltype =     length =
SEQUENCE: 31
000

SEQ ID NO: 32           moltype =     length =
SEQUENCE: 32
000
```

| | | |
|---|---|---|
| SEQ ID NO: 33 | moltype = | length = |
| SEQUENCE: 33 000 | | |
| SEQ ID NO: 34 | moltype = | length = |
| SEQUENCE: 34 000 | | |
| SEQ ID NO: 35 | moltype = | length = |
| SEQUENCE: 35 000 | | |
| SEQ ID NO: 36 | moltype = | length = |
| SEQUENCE: 36 000 | | |
| SEQ ID NO: 37 | moltype = | length = |
| SEQUENCE: 37 000 | | |
| SEQ ID NO: 38 | moltype = | length = |
| SEQUENCE: 38 000 | | |
| SEQ ID NO: 39 | moltype = | length = |
| SEQUENCE: 39 000 | | |
| SEQ ID NO: 40 | moltype = | length = |
| SEQUENCE: 40 000 | | |
| SEQ ID NO: 41 | moltype = | length = |
| SEQUENCE: 41 000 | | |
| SEQ ID NO: 42 | moltype = | length = |
| SEQUENCE: 42 000 | | |
| SEQ ID NO: 43 | moltype = | length = |
| SEQUENCE: 43 000 | | |
| SEQ ID NO: 44 | moltype = | length = |
| SEQUENCE: 44 000 | | |
| SEQ ID NO: 45 | moltype = | length = |
| SEQUENCE: 45 000 | | |
| SEQ ID NO: 46 | moltype = | length = |
| SEQUENCE: 46 000 | | |
| SEQ ID NO: 47 FEATURE misc_feature source SEQUENCE: 47 gggcgtactc cgcccaa | moltype = RNA   length = 17 Location/Qualifiers 1..17 note = P1 region sequence 1..17 mol_type = other RNA organism = synthetic construct | 17 |
| SEQ ID NO: 48 | moltype = | length = |
| SEQUENCE: 48 000 | | |

CONSTRUCT OF SELF-CIRCULARIZATION RNA

CROSS REFERENCE TO RELATED APPLICATIONS

This application is a bypass continuation-in-part of and claims benefit of PCT/KR2022/003377 filed Mar. 10, 2022, which claims priority based on Korean Patent Application No. 10-2021-0031225 filed Mar. 10, 2021, and this application claims priority based on Korean Patent Application No. 10-2022-0029918 filed Mar. 10, 2022, of which the entire contents are incorporated by reference.

INCORPORATION BY REFERENCE OF SEQUENCE LISTING

The content of the electronically submitted sequence listing, file name: Q278467_Sequence_Listing_As_Filed.xml; size: 44,809 bytes; and date of creation: Oct. 4, 2022, filed herewith, is incorporated herein by reference in its entirety.

TECHNICAL FIELD

This disclosure relates to self-circularization RNA constructs.

BACKGROUND ART

Circular RNAs (circRNAs) are single-stranded transcripts covalently linked. Through RNA-seq data and a newly developed bioinformatics approach, more than tens of thousands of circRNA types have been identified in various living organisms. In eukaryotes, it is known that a circRNA may be generated through back-splicing from mRNA and may regulate gene expression by performing a microRNA sponge function in vivo. It is not known whether a circRNA induces immunogenicity, and it exists very stably in vivo due to its structural characteristics.

Recently, the development of therapeutic agents using messenger RNA (mRNA) is active. However, mRNA has a limitation in that it is easily degraded in vivo and has a relatively short half-life. In order to overcome this limitation, studies such as attaching poly(A) tail to mRNA to improve stability are in progress. In the same vein, U.S. Pat. No. 10,953,033 discloses a circRNA for the purpose of gene expression in vivo based on the structural characteristics of the circRNA.

There are still needs to provide an RNA construct that is capable of being self-circularized via a self-targeting and splicing reaction.

SUMMARY

According to an aspect of the present disclosure, there is provided a self-circularization RNA construct having the following structure:

5'-IGS (internal guide sequence)—ribozyme—gene of interest—target site 3', wherein 5' and 3' each represent the 5-terminus and the 3'-terminus of the RNA construct, and gene of interest is an RNA sequence of an interest.

In one exemplary embodiment of the present disclosure, the IGS region form a guanine (G): uracil (U) wobble base pair, in which the guanine forming the wobble base pair may be located at the 5' end of the IGS region, and the uracil forming the wobble base pair may be located at the 3' end of the target site region.

In another example embodiment of the present disclosure, the IGS region may comprise or consist of a nucleotide sequence represented by 5'-GNNNNN-3' (SEQ ID NO: 1), and the target site region may comprise or consist of a nucleotide sequence represented by 5'-N'N'N'N'N'U-3' (SEQ ID NO: 2). Nucleotide N of the IGS region and nucleotide N' of the target site region may each independently be A, G, C, or U, but preferably, at least one nucleotide may be a nucleotide capable of forming a complementary binding between the IGS region and the target site region. In embodiments, part or entirety of the target site region may be a part of the gene of interest. For example, the IGS region may be designed to be capable of forming a reverse complementary binding to a 2-10 contiguous sequence upstream (i.e., in the 5' direction) uracil nucleotide present in the gene of interest.

In particular, the following embodiments are provided according to various aspects of the present disclosure.

Embodiment 1. A self-circularization RNA construct comprising, from the 5'-terminus to the 3'-terminus:
a) an internal guide sequence (IGS) region comprising guanine (G) at the 5'-end;
b) ribozyme region;
c) a gene of interest (GOI) region; and
d) a fragment containing target splice site comprising uracil (U) at the 3'-end,
wherein the 5'-end G of the IGS and the 3'-end U of the target splice site-containing fragment form a G: U wobble base pair, and
wherein the self-circularization RNA construct allows production of a circular RNA comprising or consisting of the gene of interest region.

Embodiment 2. The self-circularization RNA construct of Embodiment 1, wherein the ribozyme is a Group I intron ribozyme.

Embodiment 3. The self-circularization RNA construct of Embodiment 1, wherein the ribozyme does not contain an exon fragment.

Embodiment 4. The self-circularization RNA construct of Embodiment 1, wherein the target splice site region consists of the uracil, and wherein the IGS region comprises or consists of a sequence, which, except the guanine (G) forming the G:U wobble base pair, is reverse complementary to a nucleotide sequence of the 3-end region of the GOI region.

Embodiment 5. The self-circularization RNA construct of Embodiment 1, wherein the IGS region comprises or consists of a sequence, which, except the guanine (G) forming the G:U wobble base pair, is reverse complementary to a nucleotide sequence of the target splice site region, and wherein the sequence comprises 2 to 10 contiguous nucleotides.

Embodiment 6. The self-circularization RNA construct of Embodiment 1, wherein a part or entirety of the d) fragment containing target splice site comprising uracil (U) at the 3'-end is contained in the c) gene of interest region.

Embodiment 7. The self-circularization RNA construct of Embodiment 1, wherein the ribozyme comprises the nucleotide sequence of SEQ ID NO: 6.

Embodiment 8. The self-circularization RNA construct of Embodiment 1, wherein the self-circularization RNA construct further comprises a 2-nt to 20-nt contiguous nucleotide sequence extended from the 5' end guanine (G) of the IGS region, said contiguous nucleotide sequence is capable of forming a P10 helix structure.

Embodiment 9. The self-circularization RNA construct of Embodiment 1, wherein the self-circularization RNA construct further comprises a 2-nt to 20-nt contiguous nucleotide sequence extended from the 5' end guanine (G) of the IGS region, said contiguous nucleotide sequence is not capable of forming a P10 helix structure.

Embodiment 10. The self-circularization RNA construct of Embodiment 1, wherein the 5' end region of the IGS region comprises a 2-nt to 20-nt contiguous sequence that is capable of forming a P1 helix structure with a 2-nt to 20-nt contiguous sequence of the 3' end of the target splice site.

Embodiment 11. The self-circularization RNA construct of Embodiment 8, wherein the self-circularization RNA construct further comprises a 2-nt to 20-nt contiguous nucleotide sequence extended from the 3' end uracil (U) of the target splice site, said contiguous nucleotide sequence extended from the 3' end uracil (U) is capable of forming a P1 helix structure.

Embodiment 12. The self-circularization RNA construct of Embodiment 9, wherein the self-circularization RNA construct further comprises a 2-nt to 20-nt contiguous nucleotide sequence extended from the 3' end uracil (U) of the target splice site, said contiguous nucleotide sequence extended from the 3' end uracil (U) is capable of forming a P1 helix structure.

Embodiment 13. The self-circularization RNA construct of Embodiment 1, wherein the self-circularization RNA construct further comprises an antisense sequence (AS) region upstream of the IGS region and an antisense binding sequence (ABS) region capable of complementary binding to the AS region downstream of the target splice site.

Embodiment 14. The self-circularization RNA construct of Embodiment 13, wherein a length of the AS region is 10-nt to 400-nt.

Embodiment 15. The self-circularization RNA construct of Embodiment 8, wherein the self-circularization RNA construct further comprises an antisense sequence (AS) region upstream of the IGS region and an antisense binding sequence (ABS) region capable of complementary binding to the AS region downstream of the target splice site.

Embodiment 16. The self-circularization RNA construct of Embodiment 15, wherein a length of the AS region is 10-nt to 400-nt.

Embodiment 17. The self-circularization RNA construct of Embodiment 11, wherein the self-circularization RNA construct further comprises an antisense sequence (AS) region upstream of the IGS region and an antisense binding sequence (ABS) region capable of complementary binding to the AS region downstream of the target splice site.

Embodiment 18. The self-circularization RNA construct of Embodiment 17, wherein a length of the AS region is 10-nt to 400-nt.

Embodiment 19. The self-circularization RNA construct of Embodiment 9, wherein the self-circularization RNA construct further comprises an antisense sequence (AS) region upstream of the IGS region and an antisense binding sequence (ABS) region capable of complementary binding to the AS region downstream of the target splice site.

Embodiment 20. The self-circularization RNA construct of Embodiment 19, wherein a length of the AS region is 10-nt to 400-nt.

Embodiment 21. The self-circularization RNA construct of Embodiment 1, wherein the gene of interest sequence region comprises an internal ribosome entry site (IRES), a spacer sequence, or a combination thereof.

Embodiment 22. The self-circularization RNA construct of Embodiment 1, wherein the gene of interest sequence region is a coding sequence, a non-coding sequence, or a combination thereof.

Embodiment 23. A vector comprising a sequence encoding the self-circularization RNA construct of Embodiment 1.

Embodiment 24. The vector of Embodiment 23, wherein the vector comprises a promoter operably linked to a gene encoding the self-circularization RNA construct.

Embodiment 25. A circular RNA produced by the vector of Embodiment 21, wherein the circular RNA consists of the gene of interest sequence region and the 3'-end uracil (U) of the target splice site or wherein the circular RNA consists of the gene of interest sequence region that comprises the target splice site including the 3'-end uracil (U).

Embodiment 26. A cell or cell population comprising the circular RNA of Embodiment 25.

Embodiment 27. A method of producing a circular RNA in a cell population or making a cell population comprising the circular RNA, said method comprising contacting cells of the cell population with a composition comprising:

a) (1) the self-circularization RNA construct of Embodiment 1, and (2) a delivery vehicle for delivering the circular RNA to the cells, said delivery vehicle comprising a nanocarrier selected from the group consisting of a lipid, a polymer and a lipo-polymeric hybrid, b) (1) a vector comprising the self-circularization RNA construct of Embodiment 1, and (2) a delivery vehicle for delivering the vector to the cells, said delivery vehicle comprising recombinant virus or nanocarrier selected from the group consisting of a lipid, a polymer and a lipo-polymeric hybrid, or c) (1) the circular RNA produced by the vector of b), and (2) a delivery vehicle for delivering the circular RNA to the cells, said delivery vehicle comprising a nanocarrier selected from the group consisting of a lipid, a polymer and a lipo-polymeric hybrid.

Embodiment 28. A composition comprising:

a) an effective amount of the self-circularization RNA construct of Embodiment 1, a vector comprising the self-circularization RNA construct of Embodiment 1, or a circular RNA produced by the self-circularization RNA construct or the vector comprising the self-circularization RNA construct, and b) a delivery vehicle for delivering the circular RNA to a cell, said delivery vehicle comprising a nanocarrier selected from the group consisting of a lipid, a polymer and a lipo-polymeric hybrid.

BRIEF DESCRIPTION OF THE DRAWINGS

FIG. 2D shows a DNA template nucleotide sequence for producing a self-circularization RNA construct expression vector of an example embodiment of the present disclosure.

FIG. 4A shows a result of extracting RNA from the candidate 1 band and performing RT-PCR. FIG. 4B shows a nucleotide sequence analysis result of RNA extracted from the candidate 1 band.

FIG. 6A shows a structure of the self-circularization RNA construct expression vector, FIG. 6B shows a result of identifying the expression of transgene through luciferase activity assay, and FIGS. 6C and 6D show RT-PCR and nucleotide sequence analysis results verifying that the transgene is expressed in a circRNA.

FIGS. 7A to 8B show circRNA purification conditions and purification results through HPLC.

Specifically, FIG. 7A shows HPLC analysis conditions using an Ultra HPLC system.

FIG. 8B shows an electrophoresis result of fractions 7, 10, 11, 12, and 13 in which peaks are prominent in FIG. 8A.

FIG. 9 shows a structure of a self-circularization RNA including AS regions of each different length. FIG. 10 shows an electrophoresis result of a sample obtained after in vitro transcription of a vector expressing the RNA.

FIG. 11 shows a structure of self-circularization RNA including a spacer of a control group (control spacer) and poly(A) spacers of various lengths. FIG. 12 shows an electrophoresis result of a sample obtained after in vitro transcription of a vector expressing the RNA.

In FIG. 13, sequence UUGGGU is SEQ ID NO: 31, 5'-GGGGCCCAA-3' is SEQ ID NO: 44, 5'-GCG-AGUACG-3' is SEQ ID NO: 45, 5'-UUGGGUGGG-3' is SEQ ID NO: 46, and 5'-GGGCGUACUCCGCCCAA-3' is SEQ ID NO: 47.

FIG. 14 shows a nucleotide sequence of a DNA template for preparing a self-circularization RNA expression vector including only a P1 region without P10 and AS regions.

FIG. 17 shows a design of the P1 region of each different nucleotide sequence, FIG. 18 shows an electrophoresis result of a sample obtained after in vitro transcription of a self-circularization RNA expression vector having the P1 region of FIG. 17, and FIG. 19 shows an electrophoresis result of a sample obtained after in vitro transcription of a self-circularization RNA expression vector having an AU-rich P1 region and a self-circularization RNA expression vector having 2 sites for P1 formation and shows an RT-PCR electrophoresis result identifying circular RNA. In FIG. 17, the sequences are as follows: P1 helix sequences are SEQ ID NOS: 1 and 2, respectively; RZ004 variant sequences are SEQ ID NOS: 30 and 31, respectively; RZ001 variant sequences are SEQ ID NOS: 32 and 33, respectively; RZ003 variant sequences are SEQ ID NOS: 34 and 35, respectively; GC rich variant sequences are SEQ ID NOS: 36 and 37, respectively; AU rich variant sequences are SEQ ID NOS: 38 and 39, respectively; 2 Sites variant sequences are SEQ ID NOS: 40 and 41, respectively; and No Complementary P1 variant sequences are SEQ ID NOS: 42 and 43, respectively.

FIG. 20A shows that circRNA preparation is possible only with an RNA construct including only IGS, ribozyme and GOI region, and uracil base at the 3' end. FIG. 20B is a schematic diagram showing that circRNA preparation is possible only with IGS, ribozyme, and RNA constructs of the GOI region when the uracil base is included at the 3' end of a GOI, in which the generated circRNA consists only of the GOI. In other words, FIG. 20B is a schematic diagram showing that when uracil is included after 5 unique nucleotide sequences at any site in the GOI, with that part as the 3' end, the rest of the 3' end side of the GOI is sent right behind the ribozyme, so that circular RNA is configured only of the GOI without additional uracil.

DETAILED DESCRIPTION

Figure 1A:
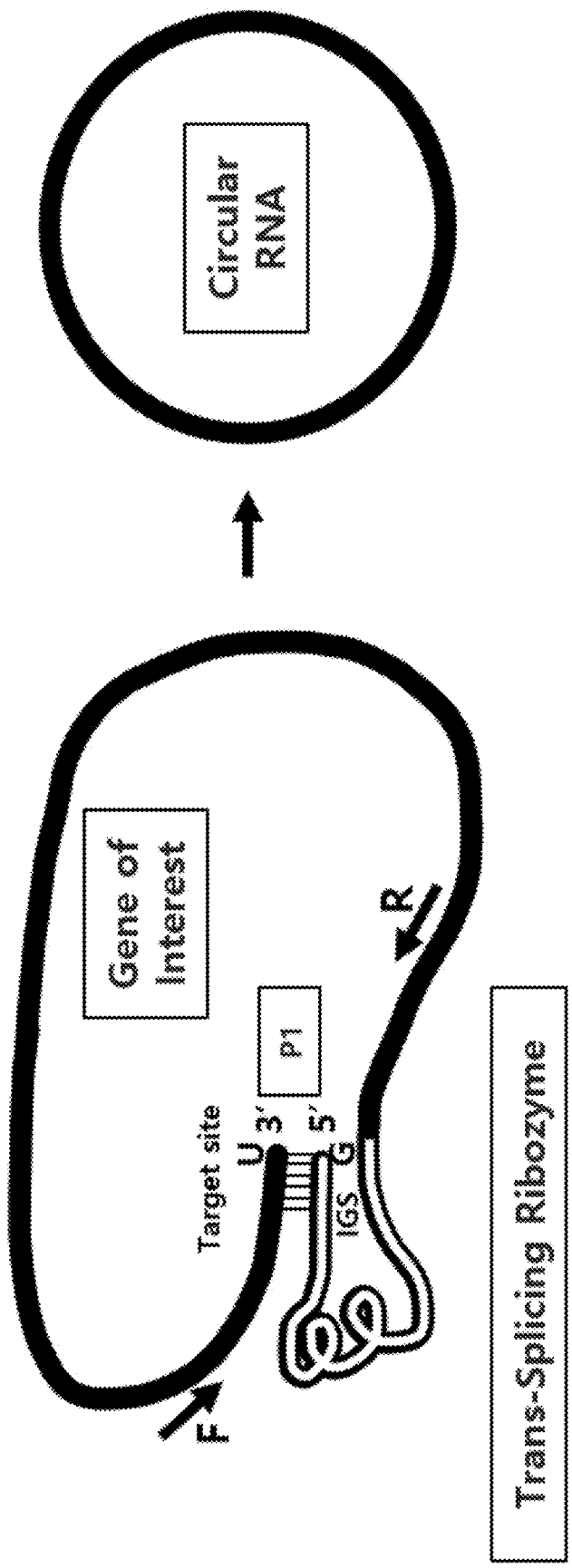
FIGS. 1A and 1B are schematic diagrams of a process in which a self-circularization RNA construct of an example embodiment of the present disclosure including only IGS, ribozyme, gene of interest, and target site region is formed into a circRNA by a self-targeting and splicing (STS) reaction.

According to an aspect, there is provided a self-circularization RNA construct comprising, from the 5'-terminus to the 3'-terminus:
  a) an internal guide sequence (IGS) region comprising guanine (G) at the 5'-end;
  b) ribozyme region;
  c) a gene of interest region; and
  d) a fragment containing target splice site comprising uracil (U) at the 3'-end,
wherein the 5'-end G of the IGS and the 3'-end U of the target splice site-containing fragment form a G: U wobble base pair, and
wherein the self-circularization RNA construct allows production of a circular RNA. As used herein, the lettering of the elements (e.g., "a.)-d.)") are used solely for clarity purposes.

In some embodiments, the ribozyme region is Group I intron ribozyme and the self-circularization RNA construct does not contain exon fragments of the Group I intron ribozyme.

In some embodiments, the fragment d) containing target splice site comprising uracil (U) at the 3'-end may be a part of the gene of interest region c). In some other embodiments, the fragment d) containing target splice site comprising uracil (U) at the 3'-end may not form the gene of interest region and located downstream of the gene of the interest region c).

In some embodiments, the a), b), c), and d) may be operably linked to each other.

According to an aspect of the present disclosure, the IGS comprises a sequence that is reverse complementary to the target splice site-containing fragment, except for G. The IGS comprises or consists of 2 to 20 nucleotides (nt). In some embodiments, IGS comprises or consists of 5 to 20 nt, 5 to 15 nt, 5 to 10 nt, 5 to 9 nt, 5 to 8 nt, 5 nt, 6 nt, 7 nt, 8 nt, 9 nt, or 10 nt, including the 5'end G. In some embodiments, the IGS comprises or consists of the sequence of SEQ ID NO: 1. In non-limiting exemplary working examples, the inventors employed IGS of SEQ ID NOs: 30, 32, 34, 36, 38, 40, or 42. The sequences of the Sequence Listing, which is incorporated by reference in the present disclosure, are described as DNA sequences for the convenience. The sequences, nevertheless, should be understood to encompass corresponding complementary RNA sequences as well, throughout the application, unless specified otherwise. Therefore, for example, the expression "the IGS of self-circularization RNA construct comprising or consisting of the sequence of SEQ ID NO: 1" should be understood as indicating an RNA sequence comprising or consisting of the RNA sequence corresponding to and complementary to the sequence of SEQ ID NO: 1.

In yet another example embodiment of the present disclosure, a nucleotide sequence of the IGS region may be reverse complementary to a nucleotide sequence of the target site region except for the guanine.

In another example embodiment of the present disclosure, the ribozyme may be a Group I intron ribozyme, and the ribozyme may comprise or consist of a nucleotide sequence represented by SEQ ID NO: 6. The ribozyme sequence contained in the self-circularization RNA construct according to embodiments of the present disclosure may not comprise exon sequences.

Figure 13:
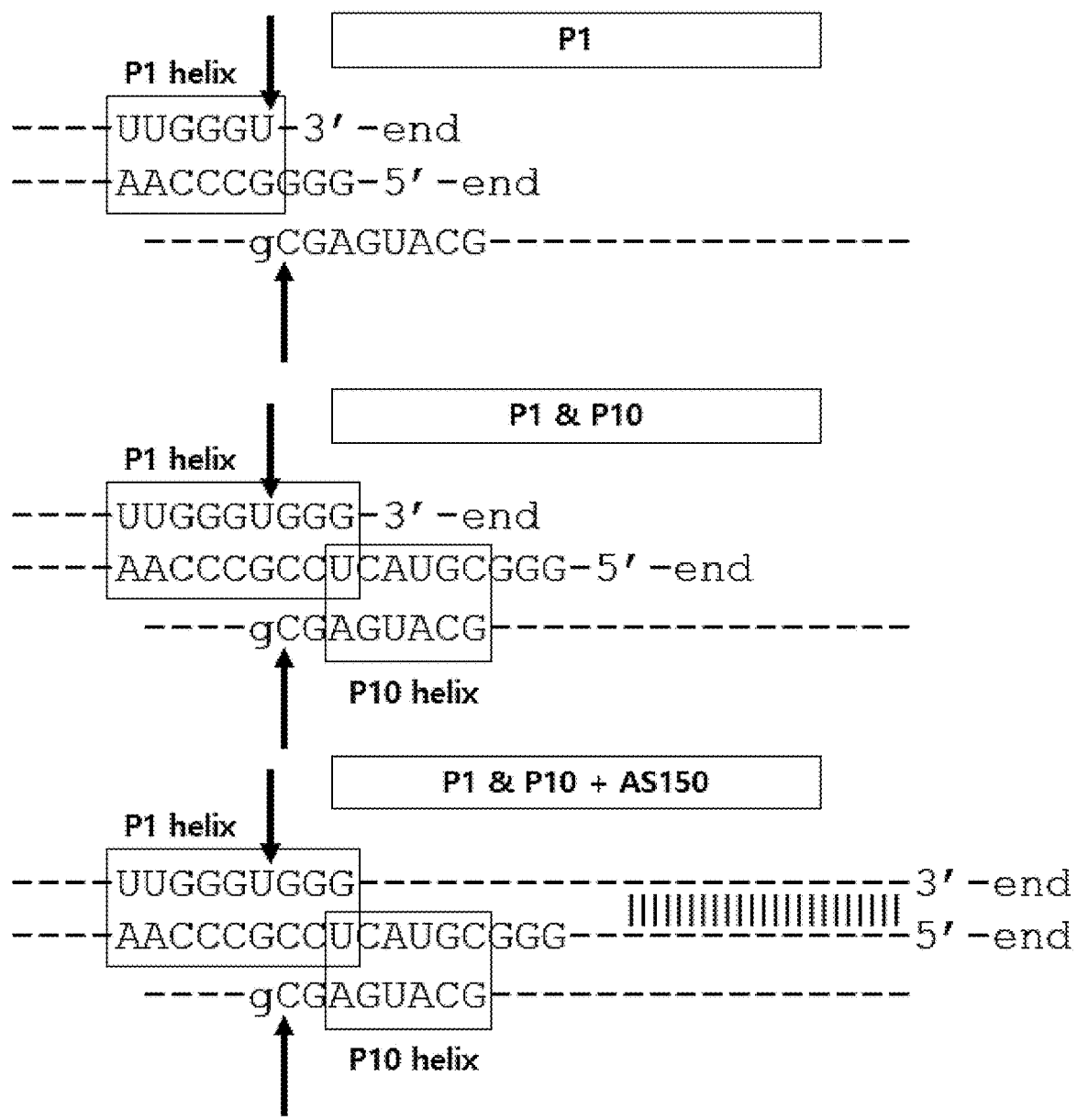
FIG. 13 indicates a nucleotide sequence near a region cleaved by a ribozyme and each region of: a self-circularization RNA including only a P1 region; self-circularization RNA including only P1 and P10 regions; and a self-circularization RNA including a P1 region, a P10 region, and an AS region.

In yet another example embodiment of the present disclosure, the self-circularization RNA construct may include a 2-20 nucleotide contiguous sequence extended from the 5' end guanine (G) of the IGS region and/or a to 2-20 nucleotide contiguous sequence extended from the 3' end uracil (U) of the target split site region, which are capable of forming a P1 helix or form a P1 and a P10 helix. See FIG. 13. As schematically shown in non-limiting exemplary illustrations of FIG. 13, the P1 helix may be formed in a region in which the complementary binding between the IGS region and the target site region is formed together with the nucleotide extended from the 3' end uracil (U) of the target site, and the P10 helix may be formed in a region in which the nucleotide extending in the 5' direction of the IGS region forms complementary binding to a sequence reverse complementary to the extended nucleotide located between ribozyme and a gene of interest (GOI) region. The length of the extended nucleotide forming the P1 helix may be from 2-nt to 20-nt, 2-nt to 15-nt, 2-nt to 10-nt, 2-nt to 9-nt, 2-nt to 8-nt, 2-nt to 7-nt, 2-nt to 6-nt, 2-nt to 5-nt, 2-nt to 4-nt, 3-nt to 9-nt, 3-nt to 8-nt, 3-nt to 7-nt, 3-nt to 3-nt, 3-nt to 5-nt, 3-nt to 4-nt, 2-nt, 3-nt, 4-nt, 5-nt, 6-nt, 7-nt, 8-nt, 10-nt, 11-nt, 12-nt, 13-nt, 14-nt, or 15-nt. In some embodiments, the length of the extended nucleotide forming the P1 helix may be 1-nt to 2-nt, 3-nt to 4-nt, 2-nt, 3-nt, 4-nt, 5-nt, 6-nt, 7-nt, 8-nt, 9-nt, or 10-nt. The length of the extended nucleotide from the 5' end guanine (G) forming the P10 helix may be 4-nt to 20-nt, 4-nt to 15-nt, 4-nt to 10-nt, 4-nt to 9-nt, 4-nt to 8-nt, 4-nt to 7-nt, 4-nt to 6-nt, 5-nt to 20-5 nt, 5-nt to 15-nt, 5-nt to 10-nt, 5-nt to 9-nt, 5-nt to 8-nt, 5-nt to 7-nt, 5-nt to 6-nt, 6-nt to 10-nt, 6-nt to 9-nt, 6-nt to 8-nt, 6-nt to 7-nt, 5-nt, 6-nt, or 7-nt. In some embodiments, the length of the extended nucleotide forming the P10 helix may be 5-nt to 7-nt, 6-nt to 7-nt, 5-nt to 6-nt, 4-nt, 5-nt, 6-nt, 7-nt, 8-nt, 9-nt, or 10-nt. In some embodiments, the extended nucleotide forming the P1 helix is 2-nt, 3-nt, 4-nt, 5-nt, 6-nt, 7-nt, or 8-nt in length and the extended nucleotide forming the P10 helix is 5-nt, 6-nt, 7-nt, 8-nt, 9-nt, or 10-nt in length. In yet another example embodiment of the present disclosure, the construct may comprise the sequence forming a P1 helix but not a sequence forming a P10 helix.

In yet another example embodiment of the present disclosure, the construct may include an antisense sequence (AS) region and an antisense binding sequence (ABS) region capable of complementary binding to each other at the 5' end and the 3' end, respectively.

In yet another example embodiment of the present disclosure, the ABS region may consist of a sequence reverse complementary to the AS region.

In yet another example embodiment of the present disclosure, the length of the AS region may vary depending on the GOI, but may be 10-nt to 500-nt. In some embodiments, the AS region may have a length ranging from 10-nt to 400-nt, 40-nt to 500-nt, 50-nt to 500-nt, 100-nt to 500-nt, 150-nt to 500-nt, 200-nt to 500-nt, 50-nt to 450-nt, 100-nt to 450-nt, 150-nt to 450-nt, 200-nt to 450-nt, 50-nt to 400-nt, 100-nt to 400-nt, 150-nt to 400-nt, 200-nt to 400-nt, 50-nt to 350-nt, 100-nt to 350-nt, 150-nt to 350-nt, or 200-nt to 350-nt.

In yet another example embodiment of the present disclosure, the GOI may include an internal ribosome entry site (IRES) region, and may include an initiation codon and a termination codon.

In yet another example embodiment of the present disclosure, the construct may further include a spacer region including a random nucleotide sequence, in which the spacer region may be located between the ribozyme region and the gene of interest region and/or between the gene of interest region and the target site region. In some embodiments, the spacer may be included as a part of the GOI and contained in the formed circular RNA.

The spacer may include or consist of poly(A), and the poly(A) is a polynucleotide in which adenine (A) is repeatedly linked, in which the A may be linked repeatedly 10 to 50 times, and preferably linked repeatedly 30 times.

In some embodiments, the target splice site-containing fragment (also referred to as "target site" or "target splice site" in, for example, drawings or sequence listing of the application), which may be reverse complementary to the IGS region, may comprise or consist of 2 to 20 nt, 2 to 15 nt, 2 to 10 nt, 5 to 20 nt, 5 to 15 nt, 5 to 10 nt, 5 to 9 nt, 5 to 8 nt, 5 nt, 6 nt, 7 nt, 8 nt, 9 nt, or 10 nt, including the 3' end U. In some embodiments, the target splice site-containing fragment comprises or consists of the sequence of SEQ ID NO: 2. In non-limiting exemplary working examples, the inventors employed the target splice site-containing fragment of SEQ ID NOs: 31, 33, 35, 37, 39, 41, or 43.

In some embodiments, the target splice site-containing fragment is the U. In this case, the 3' end of the gene of interest is contiguous to the target splice site-containing fragment U and the 3' end region of the gene of interest may have a sequence that is reverse complimentary to the IGS region.

In some embodiments, the ribozyme region may be a Group I intron ribozyme. In some embodiments, the ribozyme region may comprise or consist of the sequence of SEQ ID NO: 6.

In some embodiments, the self-circularization RNA construct may comprise a first nucleotide sequence that is a part of the 5' end region and/or extended from the 5' end of the IGS region and a second nucleotide sequence that is a part of the 3' end region and/or extended from the 3' end of the target splice site, said first nucleotide sequence and said second nucleotide sequence are capable of forming together a P1 helix structure.

In some embodiments, the self-circularization RNA construct may comprise a sequence extended from the 5' end of the IGS region, which is capable of forming a P10 helix structure. In some other embodiments, the self-circularization RNA construct may not comprise a sequence upstream (extending from the 5' end) of and adjacent to the IGS region, which is capable of form a P10 helix. Thus, according to embodiments of the present disclosure, the self-circularization RNA construct may or may not form a P10 helix, or may or may not comprise a sequence(s) (or a region(s)) forming a P10 helix. The terms "P10 helix (structure)" and "P1 helix (structure)" are explained hereinbelow.

In some embodiments, the self-circularization RNA construct may comprise an antisense sequence (AS) region upstream (in a 5' direction) of and adjacent to the IGS region and an antisense binding sequence (ABS) region capable of complementary binding to the AS region, downstream of and adjacent to the target splice site-containing fragment.

The length of AS region and the ABS region may range from 10-nt to 500-nt, depending on various factors such as the length of the GOI, the sequence of the GOI, and the like. In some embodiments, the length of the AS region and the ABS region may range from 10-nt to 500-nt, 10-nt to 450-nt, 10-nt to 400-nt, 10-nt to 350-nt, 10-nt to 300-nt, 10-nt to 250-nt, 10-nt to 200-nt, 10-nt to 150-nt, 50-nt to 500-nt, 50-nt to 450-nt, 50-nt to 400-nt, 50-nt to 350-nt, 50-nt to 300-nt, 50-nt to 250-nt, 50-nt to 200-nt, 50-nt to 150-nt, 100-nt to 500-nt, 100-nt to 450-nt, 100-nt to 400-nt, 100-nt to 350-nt, 100-nt to 300-nt, 100-nt to 250-nt, 100-nt to 200-nt, 100-nt to 150-nt, 150-nt to 500-nt, 150-nt to 450-nt, 150-nt to 400-nt, 150-nt to 350-nt, 150-nt to 300-nt, 150-nt to 250-nt, 150-nt to 200-nt, 200-nt to 500-nt, 200-nt to 450-nt, 200-nt to 400-nt, 200-nt to 350-nt, 200-nt to 300-nt, or 200-nt to 250-nt.

In some embodiments, for example, when the gene of interest region comprises a coding sequence, the gene of interest of may comprise an internal ribosome entry site (IRES) region. In these embodiments, the IRES may be located upstream (5' end) of and adjacent to the coding sequence.

In some embodiments, the gene of interest of the self-circularization RNA construct may comprise a spacer. As used herein, a "spacer" refers to any contiguous nucleotide sequence that is 1) predicted to avoid interfering with proximal structures, for example, from the IRES, gene of interest, or intron; 2) at least 7-nt long (and optionally no longer than 100-nt); and 3) located downstream of and adjacent to the ribozyme region and/or downstream of and adjacent to the gene of interest. In some embodiments, the spacer may be a poly A of at least 7-nt in length, for example 7-100 nt, 10-50 nt, or 10-30 nt. In some embodiments, the spacer may be located either or both upstream of and adjacent to and downstream of and adjacent to the gene of interest.

In some embodiments, the gene of interest of the self-circularization RNA construct may comprise an IRES sequence. The IRES sequence may be selected from various sources including, but not limited to, an IRES sequence of virus (e.g., simian virus 40, HIV virus, hepatitis virus, encephalomyocarditis virus (EMCV), human FGF2, mouse HIF1 alpha, and the like).

According to another aspect, there is provided a vector for making circular RNA, said vector comprising a self-circularization RNA construct described herein. The vector allows a production of a circular RNA that is translatable and/or biologically active inside eukaryotic cells. As used herein, the term "vector" means a piece of DNA, that is synthesized (e.g., using PCR), or that is taken from a virus, plasmid, or cell of a higher organism into which a foreign DNA fragment can be or has been inserted for cloning and/or expression purposes.

As used herein, the elements of a vector are "operably connected" if they are positioned on the vector such that they can be transcribed to form a precursor RNA that can then be circularized into a circRNA by self-targeting and self-circularization.

In an aspect, the group I intron ribozyme utilizable in embodiments of the present disclosure may comprise or consist of the sequence of SEQ ID NO: 6. In some embodiments, the group I intron ribozyme may comprise a contiguous sequence that has sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the sequence of SEQ ID NO: 6.

According to embodiments, the gene of interest region may be coding region or non-coding region. The gene of interest region can be natural or synthetic sequences. In some embodiments, the coding regions can encode mammal proteins or antibodies, chimeric antigen receptors, immunomodulatory proteins, transcription factors, mRNA vaccine, mRNA therapeutic agent, and/or gene/RNA editing enzymes such as Cas9, Cpf1, zinc finger nucleases or transcription activator-like effector nucleases (TALEN5). In some embodiments, the noncoding regions can encode sequences can alter cellular behavior, such as e.g., lymphocyte behavior. In some embodiments, the noncoding sequences may be antisense to target cellular RNA sequences. Noncoding gene of interest may be functional RNA such as miRNA, anti-miRNA, siRNA, shRNA, aptamer, guide RNA (gRNA) for gene/RNA editing, RNA for base-editing including ADAR (adenosine deaminase acting on the RNA)-recruiting RNA, vaccine adjuvant, and the like.

In some embodiments, in order to express protein (encoded by the gene of interest) in a cell or deliver the self-circularization RNA construct to a cell, the construct or vector can be transfected into the cell using, for example, lipofection or electroporation. In another embodiment, the circular RNA is transfected into a cell using a nanocarrier. The nanocarrier can be, for example, a lipid, polymer or a lipo-polymeric hybrid.

The circular RNA can be purified by the method of running the RNA through a size-exclusion column in tris-EDTA or a buffer (e.g., citrate buffer) in a high-performance liquid chromatography (HPLC) system, ion-pairing (IP) reversed phase (RP)-HPLC, anion exchange HPLC, and the like. In one embodiment, the RNA is run through the size-exclusion column in tris-EDTA or citrate buffer at pH in the range of about 4-7 at a flow rate of about 0.01-5 mL/minute.

In some embodiments, there is provided a circRNA produced from the self-circularization RNA construct or by the vector containing the same. In an aspect, the circRNA may consist of the gene of interest sequence region and the uracil (U), or the circRNA may consist of the gene of interest sequence region in which the gene of interest sequence regions comprises the target splice site including the 3'-end uracil (U).

In some embodiments, prokaryotic cells or cell populations, eukaryotic cells or cell populations, or semi-synthetic cells or cell populations, comprising the circRNA are provided.

In the present disclosure, the term "region" as used herein may mean a contiguous nucleotide sequence (e.g., RNA sequence) of a certain length. For example, the term "GOI region," "IRES region," "target site region (or splice target site region or cleavage target site region)" used herein mean nucleotide sequences (e.g., RNA sequences) of the GOI, IRES, and the sequence containing target cleavage or splicing site, respectively.

Figure 21:
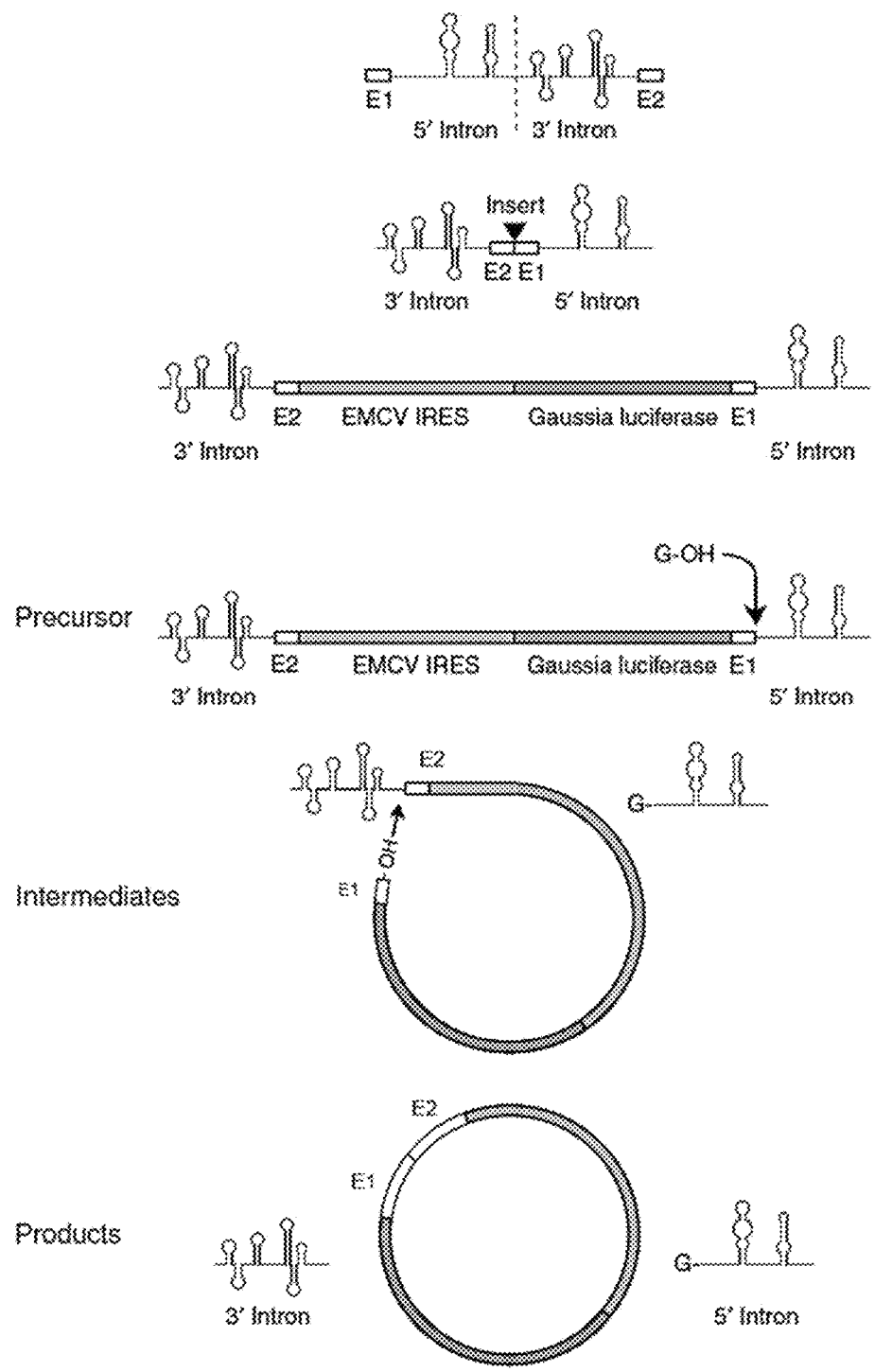
FIG. 21 is schematic diagram showing the existing permuted intron-exon construct design and mechanism of splicing as reported in Wesselhoeft et al. (2018). The group I catalytic intron of the T4 phage Td gene is bisected in such a way to preserve structural elements critical for ribozyme folding. Exon fragment 2 (E2) is then ligated upstream of exon fragment 1 (E1), and a coding region roughly 1.1 kb in length is inserted between the exon E1-exon E2 junction. During splicing, the 3' hydroxyl group of a guanosine nucleotide engages in a transesterification reaction at the 5' splice site. The 5' intron half is excised, and the freed hydroxyl group at the end of the intermediate engages in a second transesterification at the 3' splice site, resulting in circularization of the intervening region and excision of the 3' intron. The resulting circRNA product obtained in Wesselhoeft et al. contains E1 and E2 fragments.

The self-circularization RNA construct of an exemplary embodiment of the present disclosure can be expressed in a DNA vector and simultaneously circularized through a self-targeting & splicing reaction without a separate GTP treatment to form a circRNA, and the circRNA can consist only of a gene of interest and free of exon fragments of Group I intron ribozyme, contrary to an existing RNA circularization technology requiring a fused partial exon fragments flanked by half-intron sequences, which remain in the formed circRNAs (see FIG. 21). The circRNA containing the gene of interest, according to embodiments of the present disclosure, has the advantage of rapidly expressing a peptide or protein from the gene of interest, including an IRES region, an initiation codon, and a termination codon. In addition, a circRNA has a circular structure and has a stable and high half-life because 5' and 3' ends are not exposed. Accordingly, functional RNA such as miRNA, anti-miRNA, siRNA, shRNA, aptamer, guide RNA (gRNA) for gene/RNA editing, RNA for base-editing including ADAR (adenosine deaminase acting on the RNA)-recruiting RNA, mRNA vaccine, mRNA therapeutic agent, vaccine adjuvant, and CAR-T mRNA, and the like can be produced as a circRNA to have high stability in cells.

The terms used in the example embodiments are used for description purposes only, and should not be construed as being limited by these example embodiments. The terms in singular form may include plural forms unless otherwise specified. It will be understood that the terms "comprising" or "having," when used herein, specify the presence of stated features, integers, steps, operations, elements, components, or combinations thereof, but do not preclude the presence or addition of one or more other features, integers, steps, operations, elements, components, or combinations thereof.

Figure 1B:
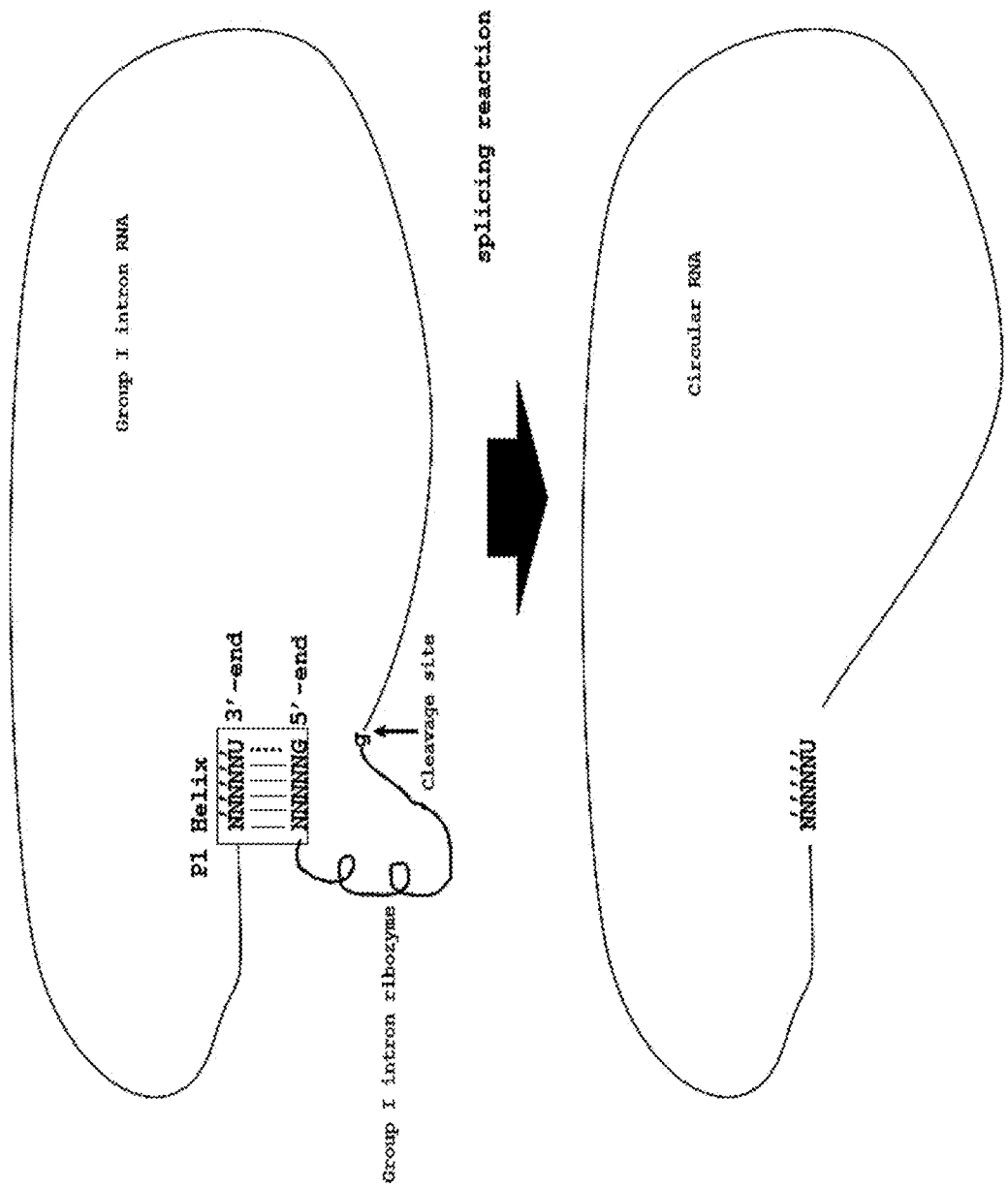

The present inventors used a trans-splicing ribozyme (T/S ribozyme) to prepare a circRNA, and devised a system in which the RNA containing a gene of interest performs a self-targeting and splicing reaction to be circularized (hereinafter referred to as "circularization system by self-targeting & splicing reaction") (FIGS. 1A and 1B).

Group I intron ribozyme may induce trans-splicing by cleaving the target RNA through two successive trans-esterification reactions and then linking separate transcripts to each other at the cleaved 3' end.

Figure 2A:
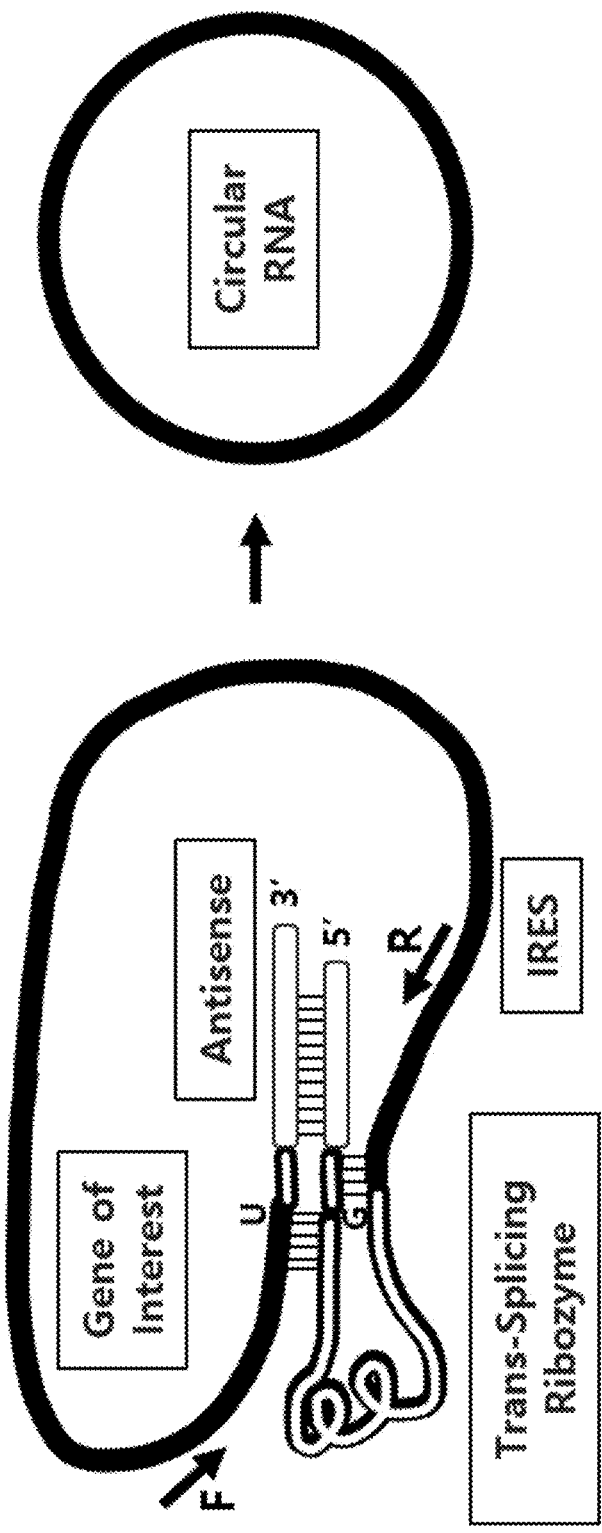
FIG. 2A is a schematic diagram of a process in which a self-circularization RNA construct of an example embodiment of the present disclosure including AS, IGS, ribozyme, gene of interest, target site, and ABS region is formed into a circRNA by an STS reaction.
Figure 2B:
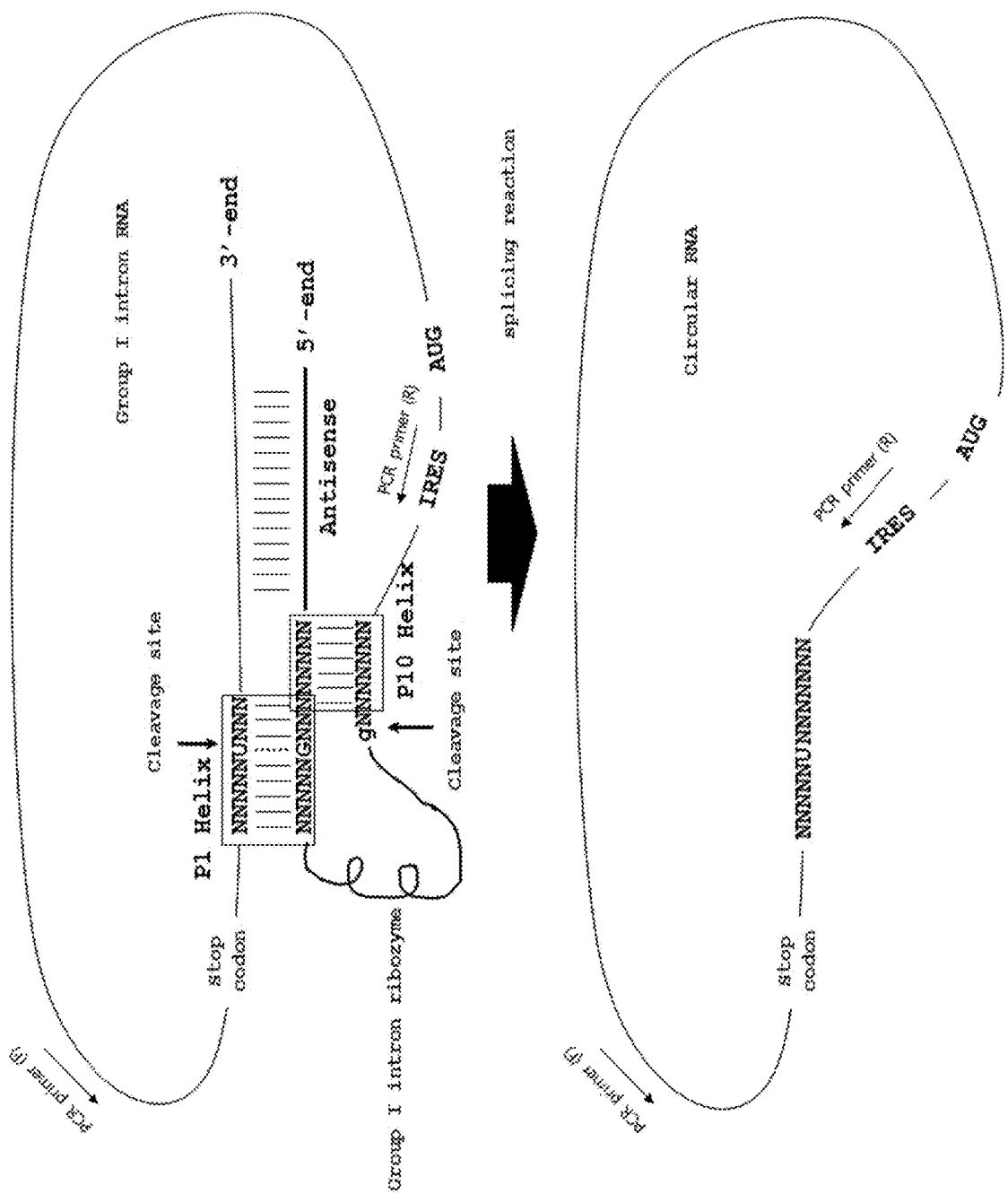
FIG. 2B is a schematic diagram of a self-circularization RNA construct of an example embodiment of the present disclosure including IRES and a termination codon in the gene of interest region to enable transgene translation, and further including nucleotides extending in a 5' direction to form P1 helix and P10 helix, and a process in which the construct is formed into a circRNA by an STS reaction.

Accordingly, in the system of an example embodiment of the present disclosure, an internal guide sequence (IGS) is configured in the 5' direction of a gene of interest (GOI) and a target site is configured in the 3' direction so that a circRNA may be produced by inducing cleavage and splicing by the ribozyme located between GOI and IGS by forming a guanine (G): uracil (U) wobble base pair so that the IGS binds complementary to the target site (FIGS. 2A and 2B).

Figure 2C:
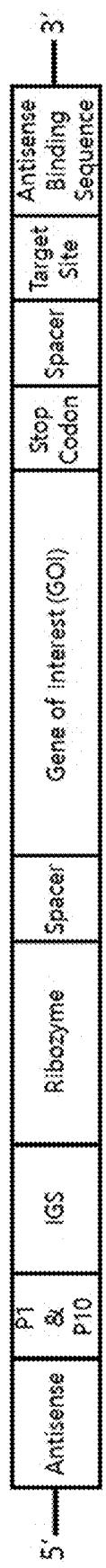
FIG. 2C shows one form of a self-circularization RNA construct of an example embodiment of the present disclosure.

For further improve the trans-splicing efficiency of Group I intron ribozyme previously reported in the previous study (Mol Ther. 2005 November; 12(5): 824-34.), and as diagrammed in FIG. 2C, the present inventors designed a self-circularization RNA construct such that an AS (antisense sequence) region and ABS (antisense binding sequence) capable of complementary binding to each other exist at the 5' and 3' ends of the self-circularization RNA construct, and P1 and P10 helixes are formed before/after the secondary structure of the ribozyme, and prepared a DNA template capable of expressing the RNA construct under a T7 promoter (Example 1).

Then, a vector into which the DNA template was inserted was produced and transcribed in vitro (IVT), and then the formation of a circRNA was identified. As a result, it was found that the vector expresses a self-circularization RNA construct, and the RNA construct forms a monomeric circRNA through a self-targeting and splicing (STS) reaction immediately after transcription even without the addition of GTP (Example 2).

Furthermore, the present inventors tested whether the self-circularization RNA construct expression vector may express the RNA construct of an example embodiment of the present disclosure even in cells, and whether the expressed RNA may express a gene of interest contained in the form of a circRNA. Specifically, a plasmid vector was produced by including IRES and a termination codon in a gene of interest to enable translation of the gene (transgene) in the cells and using gaussia luciferase as a transgene in the gene of interest, and the plasmid vector was transformed into cells to identify the production of a circRNA and luciferase activity. As a result, it was identified at the molecular level that the produced plasmid vector expressed the self-circularization RNA construct in the cells, the construct was circularized into a circRNA by ribozyme, and the gene of interest was expressed in the circRNA (Example 3).

Subsequently, the present inventors further investigated several variables such as modifications to the RNA construct to more efficiently form a circRNA through an STS (direct STS) reaction immediately on IVT.

First, the direct STS reaction rate according to a length of an AS region on IVT was identified through a specific experiment. Specifically, a self-circularization RNA expression vector was produced so that the lengths of the AS region and the ABS region were 50, 100, 150, 200, 250, or 300-nt, and the direct STS efficiency was identified after the vector was subjected to IVT. As a result, it was identified that the self-circularization efficiency was reduced at a length of 200-nt or more. Although the self-circularization efficiency was similar at 50, 100, and 150-nt lengths (and, thus, a range from about 50-nt to about 150-nt), it was identified that the in vitro transcription reaction itself decreased when the AS region and the ABS region of a 50-nt or 100-nt length are included. In terms of circRNA production efficiency, the inventors' experiment employing the particular GOI described herein show that the lengths of the AS region and the ABS region may have an influence on the circRNA production efficiency (Example 5).

Similar to the identification of the circRNA production efficiency according to the lengths of the AS region and the ABS region, the circRNA production efficiency according to the length and nucleotide sequence of a spacer region on IVT was identified. As a result, it was found that although its length and nucleotide sequence did not significantly affect the circRNA production efficiency, the linking of 30 adenines (A) was sufficient not to create a structural conflict that may occur due to a narrow gap between ribozyme and IRES (internal ribosome entry site) in the case of the ribozyme and the EMCV (Encephalomyocarditis virus) IRES (Example 6).

In an example embodiment of the present disclosure, the ribozyme was used as a Group I intron ribozyme capable of a continuous trans-esterification reaction. Group I intron ribozymes induce trans-splicing by linking separately existing transcripts to each other at the cleaved 3' end after cleavage of the target site, and link the 5' site of a GOI to the cleaved 3' end, not a separate transcript in a self-circularization RNA construct. It was intended to identify whether the P1 and P10 helix regions, known to increase trans-splicing efficiency, and the AS region and ABS region at both ends of the self-circularization RNA construct also had a positive effect on circularization efficiency.

Specifically, the present inventors produced a self-circularization RNA expression vector including only a P1 helix region, only P1 and P10 helix regions, or both the P1 and P10 helix and AS regions, and identified direct STS efficiency after IVT of the vector. As a result, surprisingly, it was found that the P10 helix region in the self-circularization RNA construct reduced the circRNA production efficiency in the presence of the P1 helix and P10 helix regions. Excellent circRNA production efficiency was exhibited even when only the P1 helix region was included without the AS region (Example 7).

Furthermore, the present inventors designed a self-circularization RNA construct so that only IGS forms a P1 helix so that only a gene of interest may be left in the final product, circRNA, and identified whether an STS reaction occurs in various IGS sequences. As a result, surprisingly, even when only the IGS region formed the P1 helix, it was identified that the STS reaction of the self-circularization RNA construct expressed in DNA was induced, and furthermore, the circRNA was formed even though the IGS region and the target site region were not complementary to each other. However, when the IGS region and the target site region are not complementary to each other, a non-specific reaction may occur at an undesired site, thereby generating an unwanted product. The IGS region of 5'-GNNNNN-3' (SEQ ID NO: 1) and the target site region of 5'-N'N'N'N'N'U-3' (SEQ ID NO: 2) showed that the circRNA production efficiency increased as the ratio of nucleotide sequences capable of complementary binding to each other increased, and that the specific sequence exhibited higher circRNA production efficiency (Example 8).

Figure 20A:
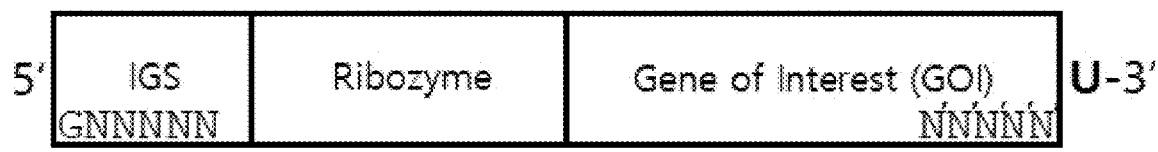
FIG. 20A and FIG. 20B are a schematic diagram of only the essential configuration of the self-circularization RNA construct.
Figure 20B:
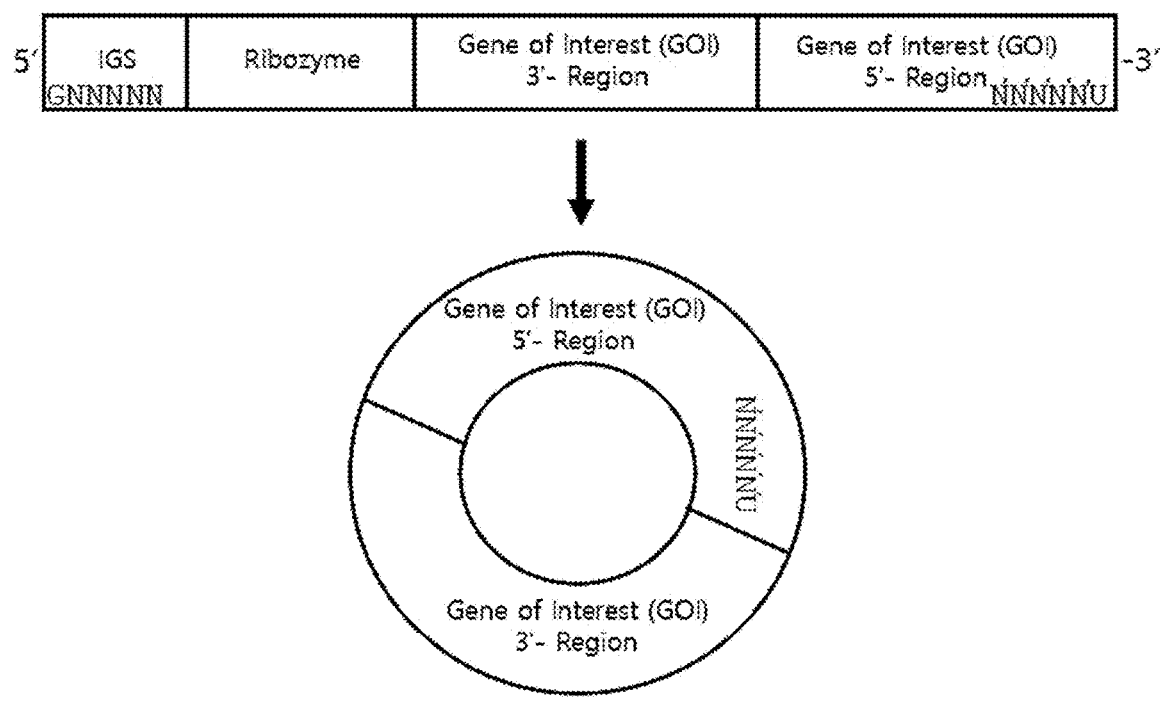

From the above, the present inventors identified that it was possible to obtain a circRNA through an STS reaction only with the RNA construct diagrammed in FIG. 1A, and the self-circularization RNA construct diagrammed in FIG. 20A may form a circRNA configured only of a gene of interest including a U base at the GOI 3' end in the circRNA precursor as shown in the schematic diagram of FIG. 20B.

When the secondary structure of the Group I intron ribozyme is formed, the nucleotide sequence linked to the upstream (5' direction) of the ribozyme and the nucleotide sequence in the 3' direction (downstream) of a transgene in which conjugation is induced by the ribozyme refer to a P1 helix structure formed through a complementary bond, and the P10 helix refers to a helix structure formed through a complementary bond between a front end region of the ribozyme and a nucleotide sequence in the 5' direction of the transcript cleaved by the ribozyme.

In an example embodiment of the present disclosure, the P1 helix may be formed through a complementary bond between the IGS at the 5' end and the target site at the 3' end in the self-circularization RNA construct, and the P10 helix refers to a helix structure formed through a complementary bond between a nucleotide sequence extended from the 5' end (upstream) and a nucleotide sequence at the downstream (3' direction) of the ribozyme.

As used herein, the nucleotide sequence forming the P1 helix is referred to as a P1 region or P1 helix region, and the nucleotide sequence forming the P10 helix is also referred to as a P10 region or P10 helix region.

In an example embodiment of the present disclosure, the nucleotide sequence of the IGS region is 5'-GNNNNN-3' (SEQ ID NO: 1), the nucleotide sequence of the target site region is 5'-N'N'N'N'N'U-3' (SEQ ID NO: 2), and the P1 helix may be formed by complementarily binding the IGS region and the target site region to each other. In this connection, in order to exclude overlapping expression, the description of the P1 helix region may be used in combination with the nucleotide sequence of the IGS region.

In an example embodiment of the present disclosure, the P1 helix may be formed including the nucleotide sequence extended in the 5' direction of the IGS region, and the nucleotide sequence of the naturally extended nucleotide sequence and the reverse complementary sequence is extended in the 3' direction of the target site to configure the P1 helix. In this connection, when the extended nucleotide sequence exists, as used herein, the extended nucleotide sequence region is denoted as P1 to distinguish the extended nucleotide sequence from the IGS region. The same goes for the P10 helix.

In an example embodiment of the present disclosure, the target site region is intended to represent a nucleotide sequence that binds complementary to the IGS region, and may overlap with the gene of interest (GOI) region according to a nucleotide sequence design of the IGS region. In this connection, in order to specify the region that binds complementary to the IGS region, the region that binds complementary to the IGS region in the gene of interest is classified and named as a target site. In other words, in an example embodiment of the present disclosure, the target site may overlap part or all of the gene of interest region, or may exist separately from the gene of interest.

In an example embodiment of the present disclosure, the AS (antisense sequence) region is located at the 5' end of the self-circularization RNA construct and aims at hydrogen bonding with the nucleotide sequence of the ABS (antisense binding sequence) region located at the 3' end of the RNA construct. In an example embodiment of the present disclosure, the AS region essentially coexists with the ABS region, and the absence of the AS region is understood to include the absence of the ABS region, and likewise, the RNA construct including the AS region is understood to also include the ABS region.

As a result of identifying the effect of the presence or absence of three types of configurations of the P1 region, P10 region, and AS region on the circularization efficiency by the STS reaction of the self-circularization RNA construct, the present inventors identified that an amount of circRNA production was large in the order of when both the P1 and P10 regions and the AS region were included, when only the P1 region was included, and when only the P1 and P10 regions were included. It was identified that the self-circularization RNA construct in the case of including only the P1 region was also circularized with sufficient efficiency to generate a circRNA. Accordingly, an example embodiment of the present disclosure provides a self-circularization RNA construct in the case of including only the P1 region.

Accordingly, as used herein, the self-circularization RNA construct including only the P1 region means that the P10 region and the AS region do not exist, and is not used in the meaning of excluding other configurations. See FIG. 3. Similarly, the self-circularization RNA construct including only the P1 region and the AS region means that the P10 region does not exist and is not used in the sense of excluding other configurations other than the P10 region. See FIG. 3.

EXAMPLES

Hereinafter, example embodiments will be described in detail with reference to the non-limiting exemplary examples. However, since various changes may be made to the example embodiments, the scope of right of the patent application is not limited or restricted by these example embodiments. It should be understood that all modifications, equivalents and substitutes for the example embodiments are included within the scope of right.

Example 1. Design of Self-Circularization RNA and Production of RNA Expression Vector The self-circularization RNA was designed as shown in FIG. 2C, and a T7 promoter sequence was additionally included for in vitro transcription reaction in the DNA template for expressing the same (FIG. 2D). The DNA template was amplified by PCR using T7 Circular Forward primer: 5'-GGGATTCGAACATCGATTAATACGACTCA-CTATAGGGGCATCGATTGAATTGT CGA-3' (SEQ ID NO: 11) (Tm=77.5° C.) and T7 Circular Reverse primer: 5'-AGATCTCTCGAGCAGCGCTGCTCGAGGCAAGC-TT-3' (SEQ ID NO: 12) (Tm=79.4° C.). The DNA template amplification product was inserted into the pTOP TA V2 cloning vector (Enzynomics) using PstI restriction enzyme to produce a self-circularization RNA expression vector.

Example 2. Identification of In Vitro Transcription and Self-Circularization 2-1. In Vitro Transcription (IVT)

The self-circularization RNA expression vector produced in Example 1 above was transcribed in vitro using NEB's HISCRIBE™ T7 high yield RNA synthesis kit according to the manufacturer's protocol. Specifically, after 3 hours of reaction at 37° C. with 20 uL scale (1 ug T7 DNA template, 1× Reaction buffer, 10 mM each ATP, UTP, CTP, GTP, T7 RNA polymerase mix 2 ul), 29 uL of nuclease-free water was added, and then 1 uL of RNase-free DNase I (10 U/ul) was added and reacted at 37° C. for 30 minutes to induce an immediate circularization (direct STS) reaction after transcription.

Subsequently, an additional circularization reaction was induced to identify the stage in which the self-circularization reaction was completed. Specifically, in order to induce the first self-targeting and splicing ($1^{st}$ STS) reaction, 28 uL of nuclease-free water and 20 uL of 5×STS buffer (50 mM Hepes (pH 7.0), 150 mM NaCl, 5 mM $MgCl_2$), 2 uL of 100 mM GTP (final 2 mM) were further added to make a volume of 100 uL, followed by self-circularization reaction at 37° C. for 1 hour. Then, after heating at 55° C. for 15 minutes, column purification was performed using a Monarch RNA cleanup kit (NEB). A second STS ($2^{nd}$ STS) reaction was induced by adding 20 uL of 5×STS buffer, 100 mM GTP (final 2 mM), and 28 uL of nuclease-free water to 50 uL of the column-purified sample again to make a final 100 uL and performing a reaction at 37° C. for 3 hours. After the reaction, heating was performed at 55° C. for 8 minutes, then column purification was performed using a Monarch RNA cleanup kit (NEB), and the concentration was measured using Nanodrop (Thermo Fisher Scientific product) equipment.

In order to remove linear RNA from the reaction product, some of the column-purified samples after the first and second STS reactions were treated with RNase R. Specifically, 10 uL of 10× RNase R reaction buffer (10×: 0.2 M Tris-HCl pH 8.0, 1 M KCl, 1 mM $MgCl_2$) and RNase R 20 Unit were added to column-purified IVT RNA of up to 100 ug (adjusting the volume to 100 uL with water) at 37° C. for 30 minutes, and then RNase R 10 unit was further added for performing a reaction for another 30 minutes. Then, column purification was performed using a Monarch RNA cleanup kit (NEB) and a concentration was measured with Nanodrop.

250 ng each of the samples treated with RNase R on RNA obtained from each STS stage and RNA obtained from each stage was mixed 1:1 with 10 M Urea-BPB (1×TBE) dye, heated at 75° C. for 5 minutes, and then 4% polyacrylamide-7 M urea denature PAGE (2 hours of electrophoresis at 50 W conditions while maintaining a temperature at 50° C.) was performed, and the gel was stained with an SYBR Gold Nucleic Acid Stain product (Thermo Fisher Scientific) and analyzed using IMAGEQUANT™ 800 (Cytiva product).

Figure 3:
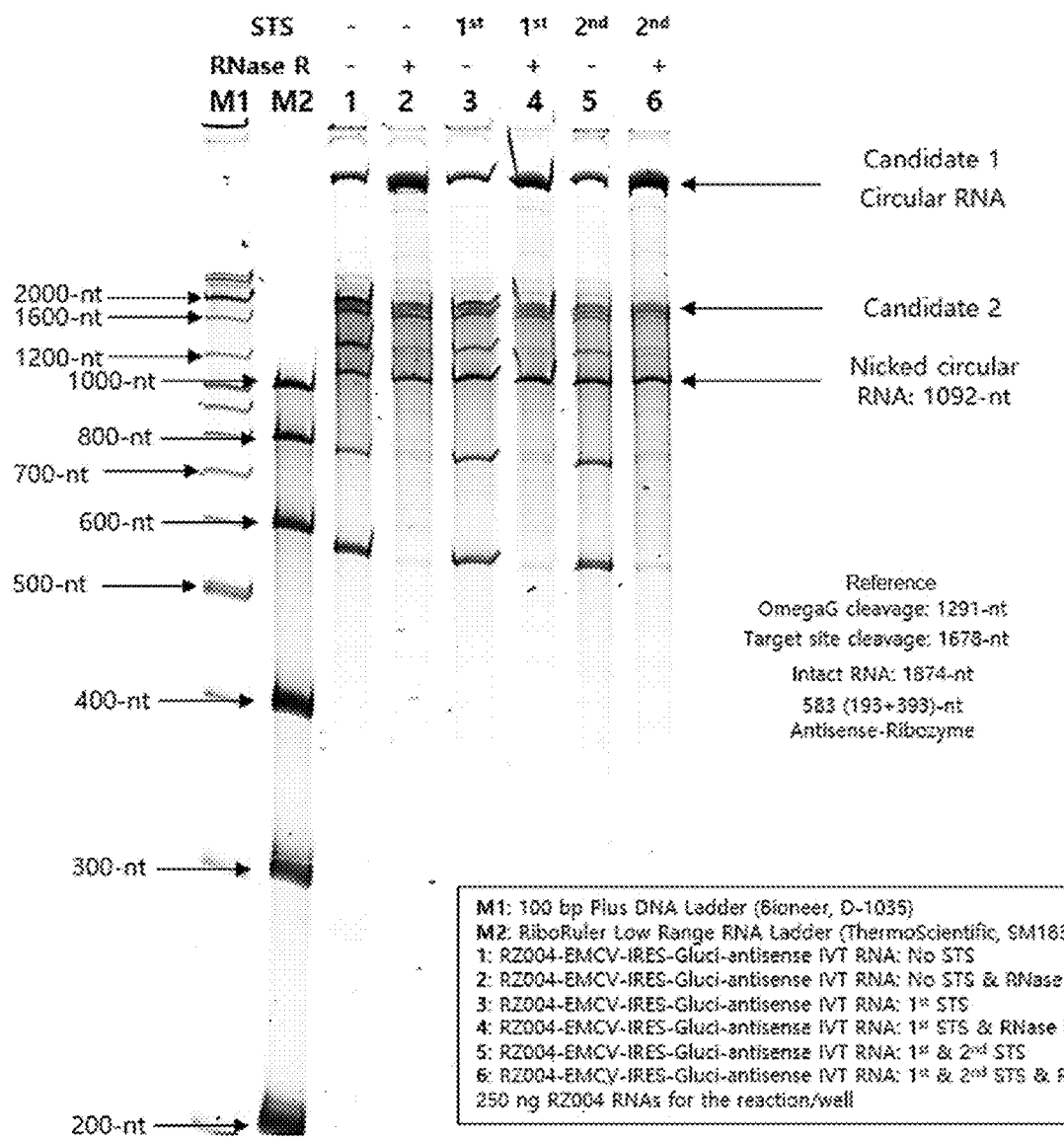
FIG. 3 shows the results of electrophoresis on a polyacrylamide gel to identify that a circRNA is generated immediately after in vitro transcription of the self-circularization RNA construct expression vector of an example embodiment of the present disclosure, without additional GTP treatment. Samples obtained immediately after transcription (direct STS) and samples after the first and second STS reaction stages in which additional GTP is treated to induce primary and secondary circularization reactions were used, and a portion of each sample was treated with RNase R to remove linear RNA, and a circRNA in the samples was concentrated and electrophoresed.

As a result, as can be seen in FIG. 3, when RNase R was treated, RNA bands that were not well cleaved by RNase R and thus were enriched were revealed (Candidate 1). In addition, bands that were clearly observable despite RNase R treatment were identified (bands presumed to be Candidate 2 and Nicked circular RNA). In addition, it was already identified that even without additional 1st and 2nd STS reactions, substances presumed to be circRNAs were sufficiently prepared only by a direct STS reaction, that is, an in vitro transcription reaction.

2-2. Identification of Self-Circularization

Subsequently, RT-PCR sequencing was performed to verify that Candidate 1 was a circRNA among the RNA bands not cleaved by RNase R from the PAGE results. Specifically, RT-PCR was performed using primers capable of PCR amplification only when circRNAs were made using a circular RNA sample purified by ethanol precipitation by cutting and crushing the band at Candidate 1 position in the PAGE and eluting the band in water at 37° C. for 3 to 16 hours and a linear RNA that does not allow circularization due to the absence of a ribozyme site and an antisense site as controls.

For reverse transcription (RT), ONESCRIPT PLUS™ RTase (Abm) was used, and 125 ng of each RNA (a sample with or without RNase R treatment on RNAs presumed to be control RNA and circular RNA) was heated at 70° C. for 5 minutes. Thereafter, the sample was put on ice, and was added with 5× RT buffer 4 uL, 10 mM dNTP mix 1 uL, 2 uM reverse primer (Circular STS R) 1 uL, and ONESCRIPT PLUS™ RTase 200 U in an orderly manner. Then, the sample was reacted at 50° C. for 15 minutes in a final volume of 20 uL, heated at 95° C. for 5 minutes to inactivate the enzyme, and then stored on ice.

Figure 4A:
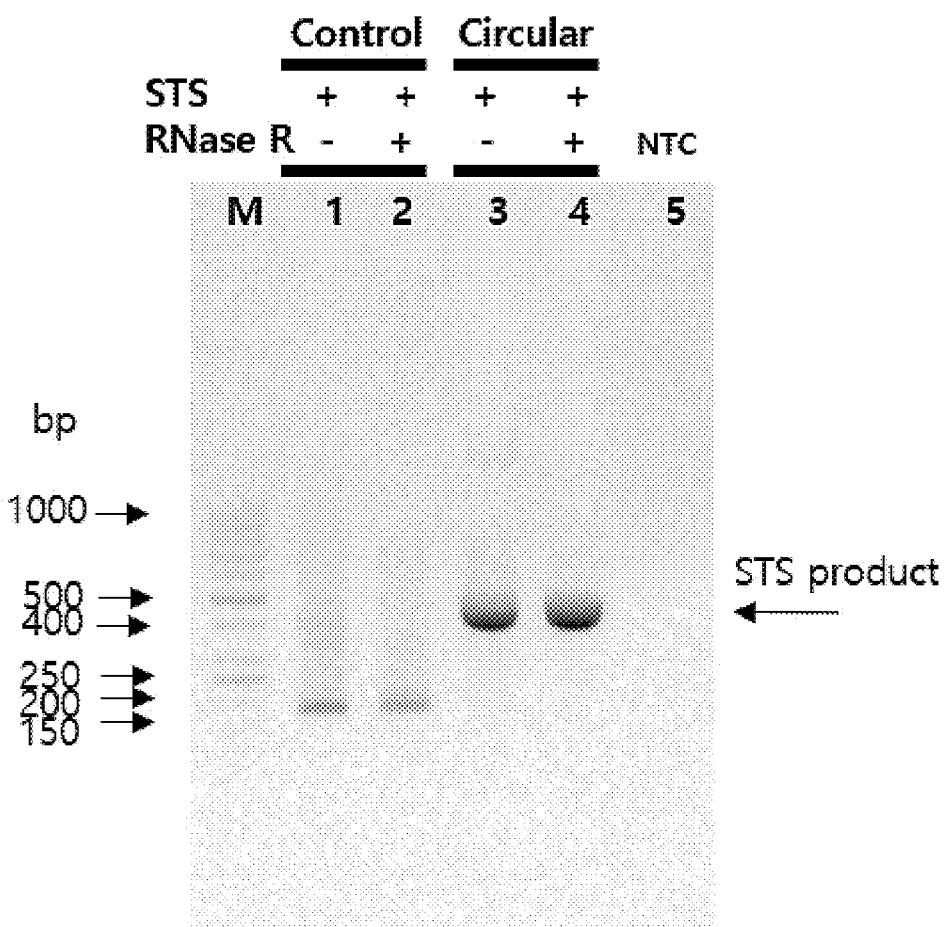
FIG. 4A and FIG. 4B are a verification that Candidate 1, which is assumed as a circRNA, is a circRNA from the results of FIG. 3.

Subsequently, PCR was performed using ACCUPOWER TAQ™ PCR premix (Bioneer), 2 uL of an RT sample and 1 uL each of 20 uM of Circular STS F (5'-CCCT-GAGTGGCTGAGCTCAGG-3') (SEQ ID NO: 13) and Circular STS R (5'-CAGCAAGCATACTAAATTGCCAG-3') (SEQ ID NO: 14) were added and adjusted to a volume of 20 uL with water, and PCR amplification was performed under the conditions of 95° C. for 1 minute, [95° C. for 30 seconds, 65° C. for 30 seconds, and 72° C. for 30 seconds], 35 cycles, and 72° C. for 5 minutes. 5 uL of a PCR product was put into 1 uL of 6×DNA loading dye, electrophoresed at 150 V for 35 minutes, and images were analyzed using a gel imaging system (Davinch-Gel product of Youngin Scientific). The expected length of the STS PCR product was 479 bp, and when analyzed by GENERULER™ 50 bp DNA ladder (Thermo Fisher Scientific) on 1.5% agarose gel (Intron Bio's product, RedSafe Nucleic Acid Staining Solution, is contained in a concentration of 1×), only in the case of an RNA sample presumed to be circular RNA, a specific PCR product of a predicted size was observed regardless of RNase R treatment (FIG. 4A).

Figure 4B:
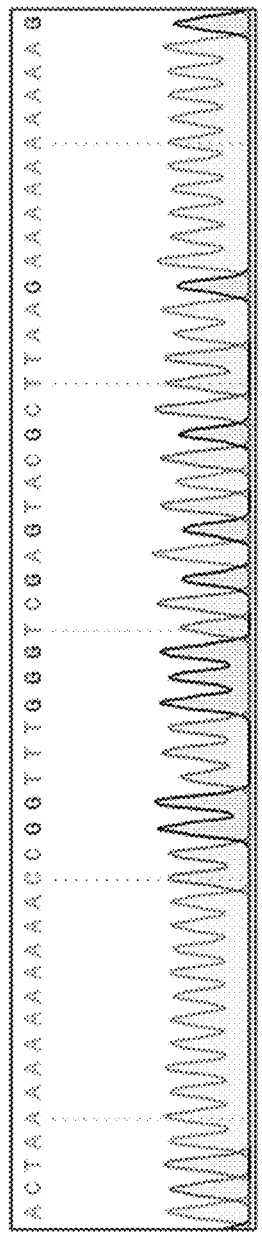

In addition, the PCR product was isolated and purified according to the manufacturer's protocol using a gel extraction kit (Cosmogenetech product) from the band of the expected size obtained, and cloned using a TOPCLONER™ TA-Blunt kit (Enzynomics product). DH5alpha *E. coli* (Chemically competent *E. coli*, Enzynomics product) was transformed to obtain *E. coli* colonies from LB-Agar (including Kanamycin) plates, and plasmid DNA was extracted and purified according to the manufacturer's protocol using a DNA purification kit (Cosmogenetech product). As a result of requesting sequencing (using M13R (−40) or M13F (−20) universal primer provided by Sanger sequencing service company of Cosmogenetech), it was identified that 3' of *Gaussia* Luciferase and 5' of IRES were correctly linked at an STS junction site (FIG. 4B).

From the above results, it was confirmed that Candidate 1 was a circular RNA.

2-3. Revalidation of Self-Circularization

It was identified that Candidate 1 is a circRNA through RT-PCR, but theoretically, the possibility that Candidate 1 is in the form of a dimer may not be excluded. Accordingly, a nicking test was performed to re-verify that Candidate 1 was a circRNA.

$MgCl_2$ was mixed with purified circular RNA candidates 1 and 2 (100 ng) to the final 0, 2.5, and 5 mM, respectively, and the sample in the final 10 uL of water was heated at 65° C. for 30 minutes and then stored on ice for a while, and then was mixed with 10 uL of 10 M Urea-BPB (1×TEB) loading dye.

Figure 5:
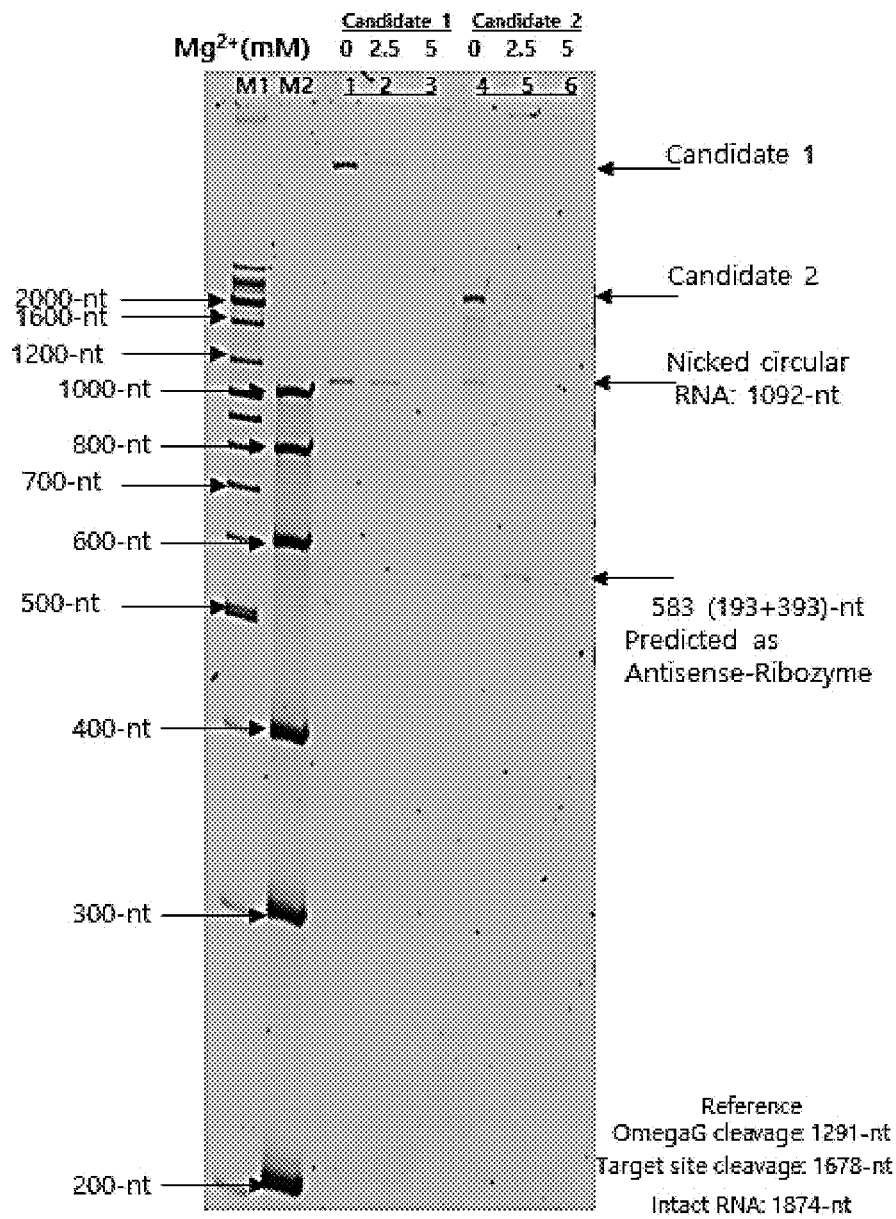
FIG. 5 is a verification that the RNA of the candidate 1 band from the results of FIG. 4 is a monomer, and shows the results of electrophoresis after extracting RNA from candidate 1 and 2 bands assumed as circRNAs from the results of FIG. 3 and inducing nick by treatment with $Mg^{2+}$.

After heating at 75° C. for 5 minutes, 4% polyacrylamide-7 M urea denature PAGE (2 hours of electrophoresis at 50 W conditions while maintaining a temperature at 50° C.) was performed, and gels were stained with an SYBR Gold Nucleic Acid Stain product (Thermo Fisher Scientific) and analyzed using IMAGEQUANT™ 800 (Cytiva product). The results are shown in FIG. 5.

It was identified that in the case of Candidate 1, in the absence of $Mg^{2+}$, a band with a size corresponding to a slight nicked circular RNA was included (1092-nt), and in the case of a 2.5 mM $Mg^{2+}$ condition, the band at the position of Candidate 1, considered the position of a circular RNA, decreased. In addition, it was identified that a band of nicked circular RNA size was still present. In the case of a 5 mM $Mg^{2+}$ condition, it was identified that even the nicked circular RNA band disappeared by hydrolysis. Thus, it was observed that Candidate 1, that is, circular RNA, proceeded from the size of 1092-nt expected as a monomer when nicking occurred (2.5 mM $Mg^{2+}$) and eventually completely degraded (5 mM $Mg^{2+}$). Accordingly, it was identified again that Candidate 1 was a circular RNA and a monomer.

Candidate 2 has a size similar to the intact RNA size of 1874-nt (around 2000-nt of the marker). Under mild nicking conditions of 2.5 mM $Mg^{2+}$, unlike Candidate 1, it was identified that the 1092-nt band, the size of the nicked circular RNA, was not generated and disappeared, and thus that it was not a circular RNA.

Example 3. Identification of Intracellular Transcription and Self-Circularization In Example 2, it was identified that the self-circularization RNA expression vector produced in Example 1 was transcribed in vitro to form a circRNA. Accordingly, it was intended to identify whether the vector also operated the same in cells, and furthermore, whether the gene of interest included in the circRNA was expressed smoothly in the cells.

For the expression of a gene of interest in cells, the gene of interest is designed with the structure of 5'-EMCV IRES-transgene-stop codon-3', and for easy identification of the expressed gene of interest, gaussia luciferase (G.luci) was used as a transgene.

Figure 6A:
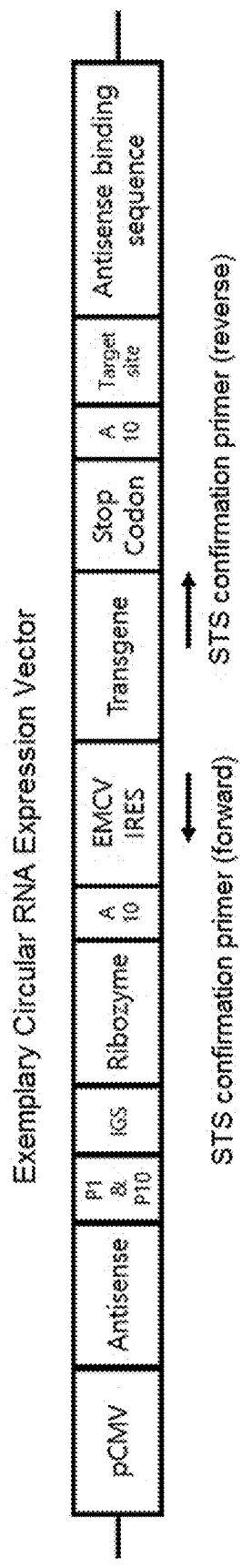
FIGS. 6A to 6D show a result of identifying that the self-circularization RNA construct expression vector of an example embodiment of the present disclosure generates a circRNA in cells and the transgene included in the circRNA is expressed. Specifically.

The self-circularization RNA construct including the aforementioned gene of interest was designed, and a DNA template, which may express the same, was inserted into a plasmid to be expressed under a pCMV promoter (FIG. 6A). The plasmid vector was transfected into 293A cells, the generation of a circRNA was identified by RT-PCR and sequencing, and the expression of transgene was identified by performing luciferase activity assay.

Figure 6C:
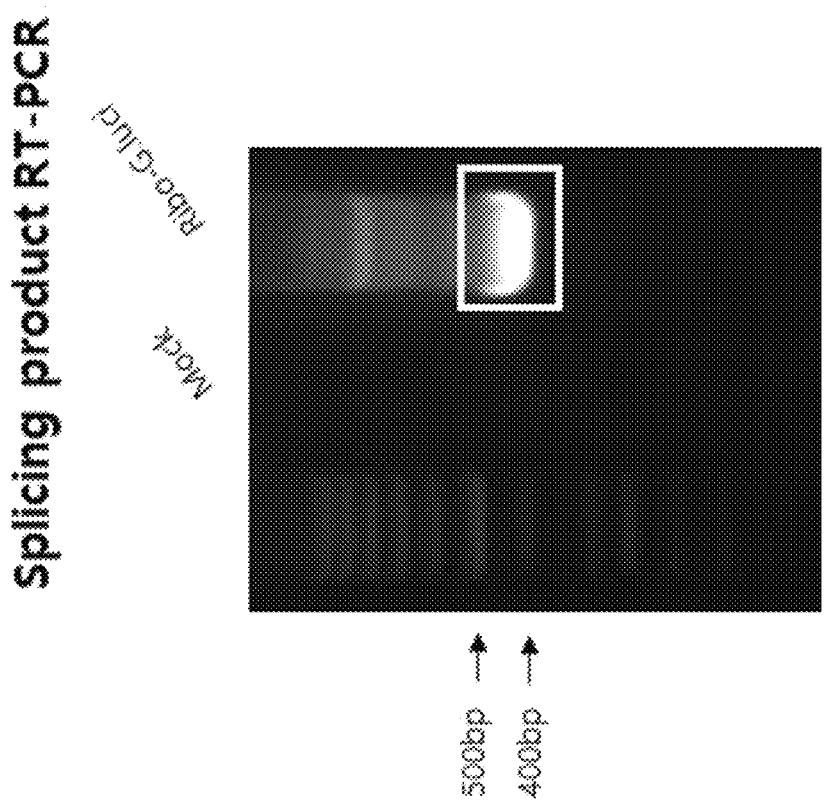
Figure 6B:
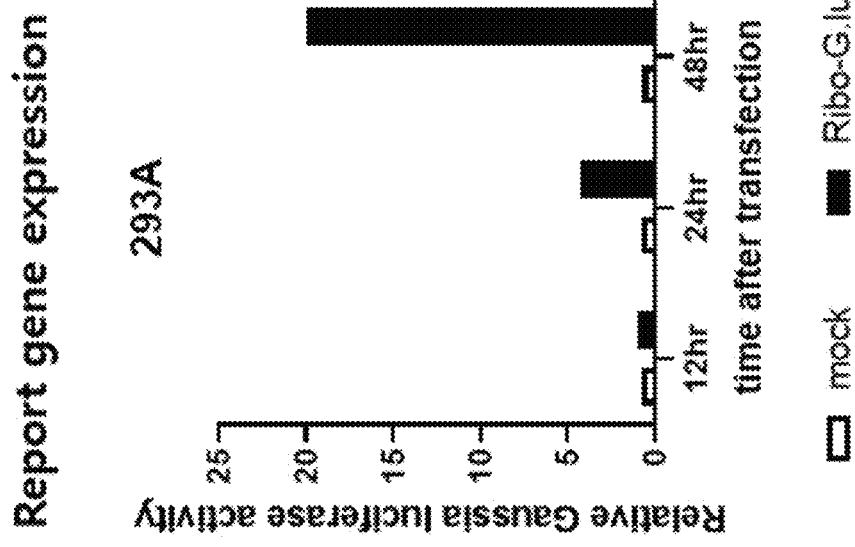

Specifically, 293A cells were seeded at 2×10⁵/well in 6 well plates and were transformed into the plasmid vector using a LIPOFECTAMINE™ 2000 transfection reagent after 24 hours. After 6 hours of transformation, a culture medium was replaced. After the transformation, 100 UL of culture medium was collected at 12, 24, and 48 hours to measure G. luci activity. It was identified that G.luci activity was detected in the culture medium and the activity increased over time, and thus it was identified that the transgene G. luci gene was expressed in the vector introduced into the cells (FIG. 6B).

It was identified at the molecular level through RT-PCR and sequencing whether transgene expression was caused by the formation of a circRNA. 48 hours after transformation, total RNA was extracted from the 293A cells introduced with the plasmid vector using trizol reagent, and then it was identified that circular RNA was generated by performing RT-PCR.

For reverse transcription (RT), ONESCRIPT PLUS™ RTase (Abm product) was used, and 1 ug of total RNA was heated at 70° C. for 5 minutes and then placed on ice. Then, 5× RT buffer 4 uL, 10 mM dNTP mix 1 uL, 2 uM reverse primer (Circular STS R) 1 uL, ONESCRIPT PLUS™ RTase 200 U were added in an orderly manner, and the final volume of 20 uL was reacted at 50° C. for 15 minutes, heated at 95° C. for 5 minutes to inactivate the enzyme, and then stored on ice.

Subsequently, PCR was performed using ACCUPOWER TAQ™ PCR premix (Bioneer product), 2 uL of an RT sample and 1 uL each of 20 uM of Circular STS primer F (5'-caaggacttggagcccatggagcag-3') (SEQ ID NO: 15) and primer R (5'-tgtgccgcctttgcaggtgtatc-3') (SEQ ID NO: 16) were added, adjusted to a volume of 20 uL with water, and PCR amplification was performed under the conditions of 95° C. for 1 minute, [95° C. for 30 seconds, 65° C. for 30 seconds, and 72° C. for 30 seconds] 35 cycles, and 72° C. for 5 minutes. A specific PCR product of the predicted size was identified only when the expected length of the STS PCR product was 479 bp and circular RNA is present when analyzed by GENERULER™ 50 bp DNA ladder (Thermo Fisher Scientific product) in 1.5% agarose gel (Intron Bio's product, REDSAFE™ Nucleic Acid Staining Solution, is contained in a 1× concentration). In this connection, 5 uL of PCR product was put into 1 uL of 6×DNA loading dye, and electrophoresed at 150 V for 35 minutes, and then the image was analyzed with a gel imaging system (DAVINCH™-Gel product of Youngin Scientific) (FIG. 6C).

Figure 6D:
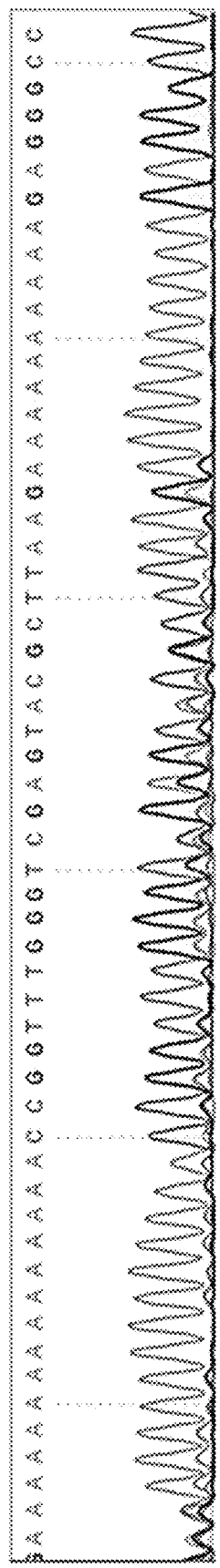

In addition, as to the obtained band of the expected size, the PCR product was isolated and purified according to the manufacturer's protocol by using a gel extraction kit (Cosmogenetech product), cloned using TOPCLONER™ TA-Blunt kit (Enzynomics product), and transformed into DH5alpha E. coli (Chemically competent E. coli, Enzynomics product) to obtain E. coli colonies on LB-Agar (including Kanamycin) plates, and extract and purify plasmid DNA using a DNA purification kit (Cosmogenetech product) and manual. As a result of the sequencing request (using M13R (−40) or M13F (−20) universal primer provided by Sanger sequencing service company of Cosmogenetech Inc.), it was identified that the 3' of Gaussia Luciferase and the 5' of the IRES were precisely linked nucleotide sequences at the STS junction site (FIG. 6D).

From the above, it was identified at the molecular level that the produced plasmid vector expressed a self-circularization RNA construct in cells, the construct was circularized into a circRNA by ribozyme, and a gene of interest was expressed in the circRNA.

Figure 7B:
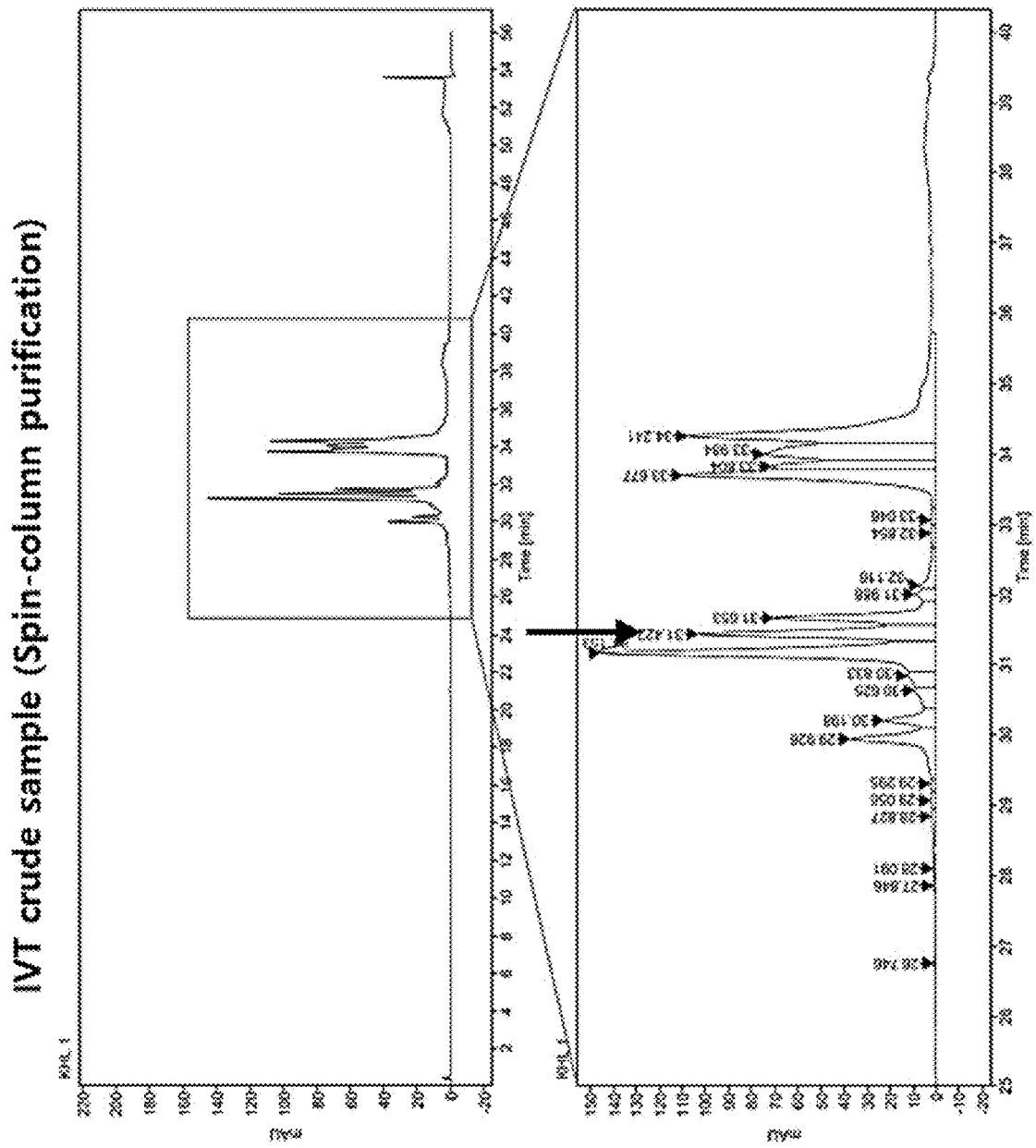
FIG. 7B shows a result of column purification of a sample obtained immediately after in vitro transcription.

Example 4. circRNA Purification 4-1. Identification of circRNA Purification Potential by Performing HPLC In order to minimize the occurrence of immunogenicity in the production of a circRNA for human injection, analysis and purification using HPLC were performed. Specifically, an Agilent 1290 Infinity II Bio UHPLC system was used and the analysis conditions are as shown in FIG. 7A. For analysis, the gradient conditions of [Analytical] were used, and the conditions of [Fraction collection] were used for sample fraction.

Figure 7C:
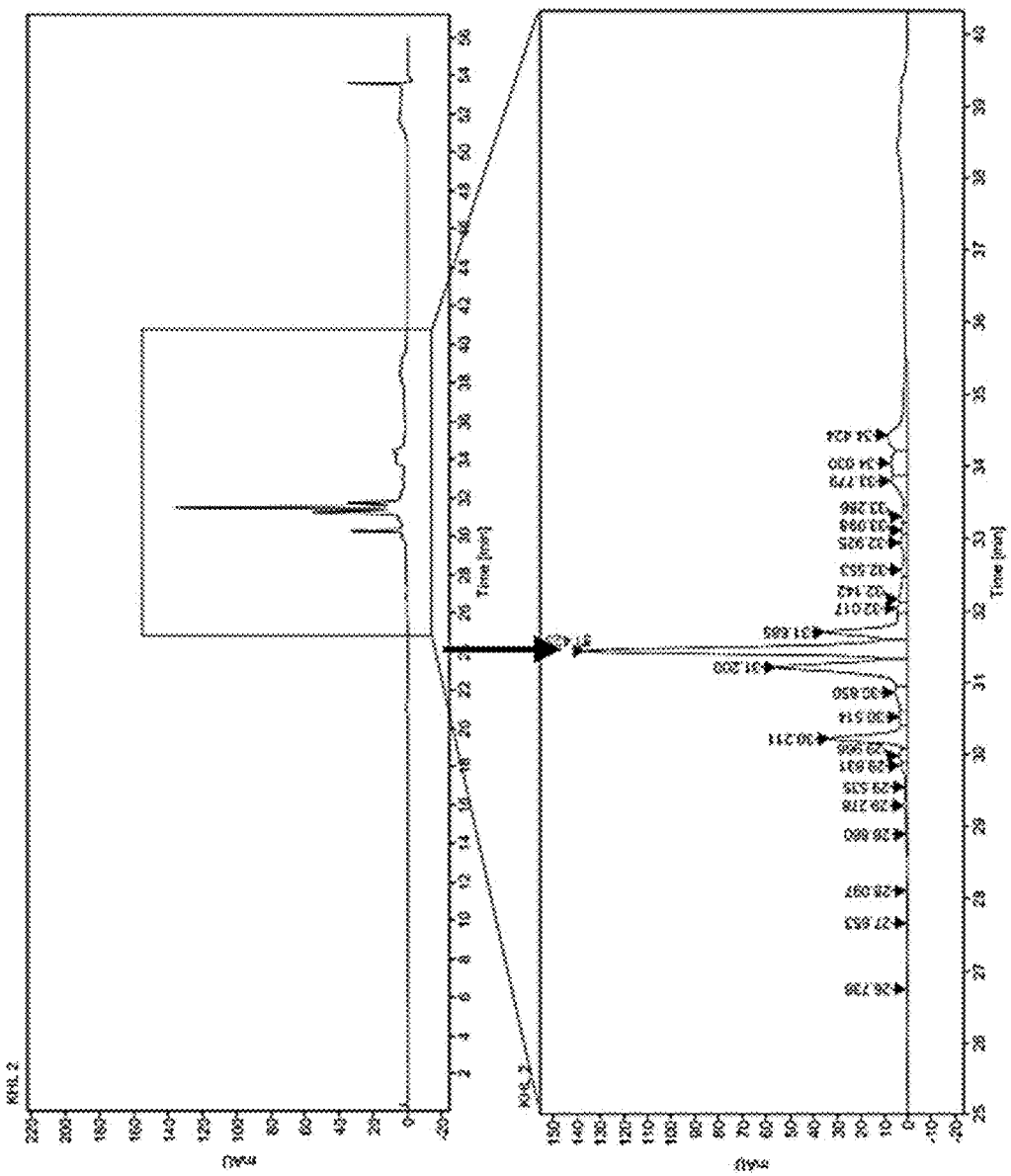
FIG. 7C shows a result of column purification after treating the sample with RNase R.

When RNA purified only with a column (a MONARCH™ RNA cleanup kit (NEB)) after IVT (FIG. 7B) and RNA treated with RNase R (FIG. 7C) were analyzed, it was found that there was an increasing peak in the RNase R-treated sample, and that a circRNA could be isolated by HPLC without RNase R treatment.

4-2 Purification of circRNA by Performing HPLC

Figure 8A:
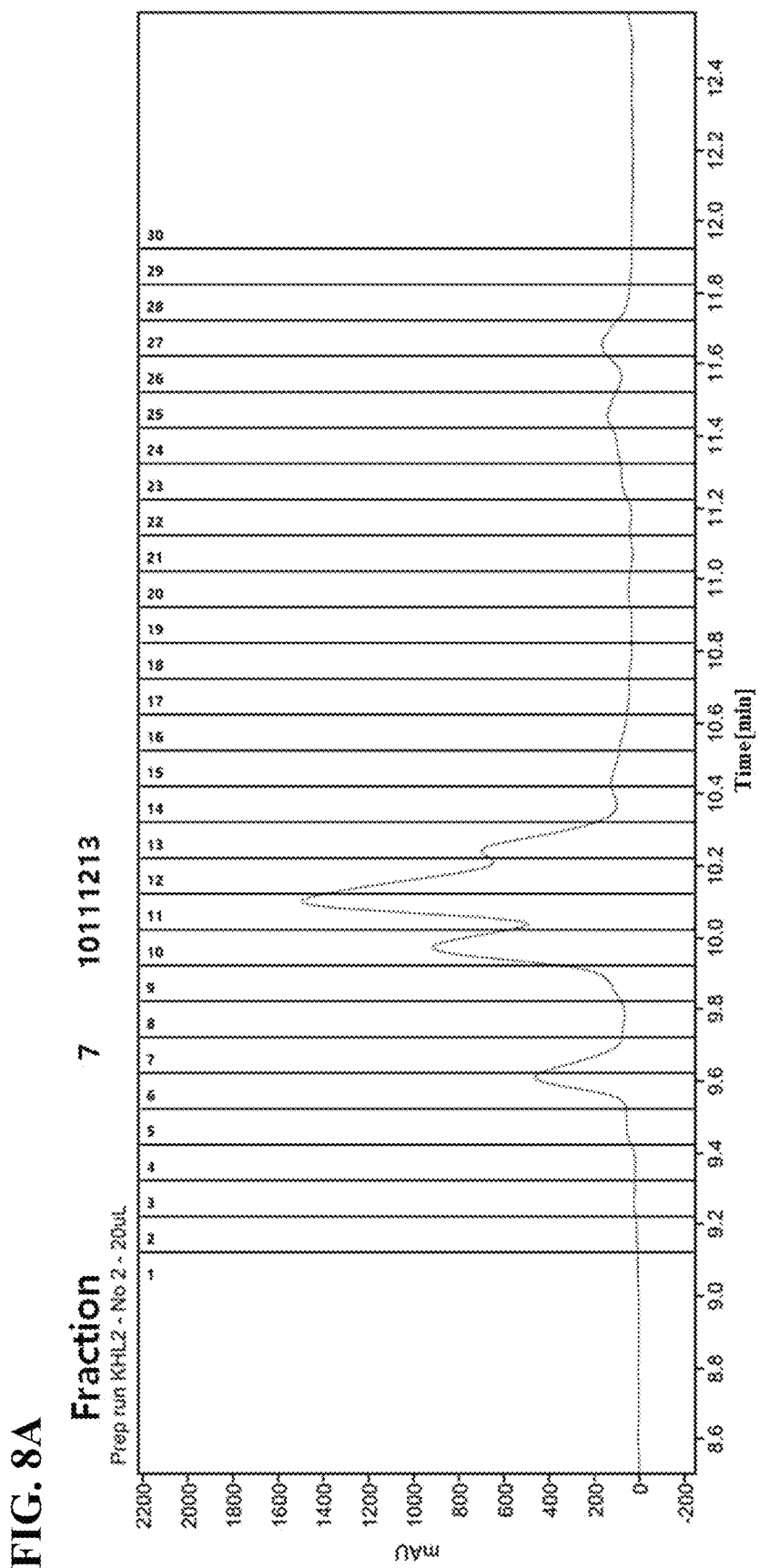
FIG. 8A shows a result of identifying a peak in the fraction obtained through column purification.

Through HPLC, fraction was performed using the gradient shown in the fraction collection conditions, and each fraction was obtained as shown in FIG. 8A. Electrophoresis was performed in the same manner as in the previous method by taking 200 ng each of fractions 7 and 10 to 13 with clear peaks on 4% denature PAGE.

Figure 8B:
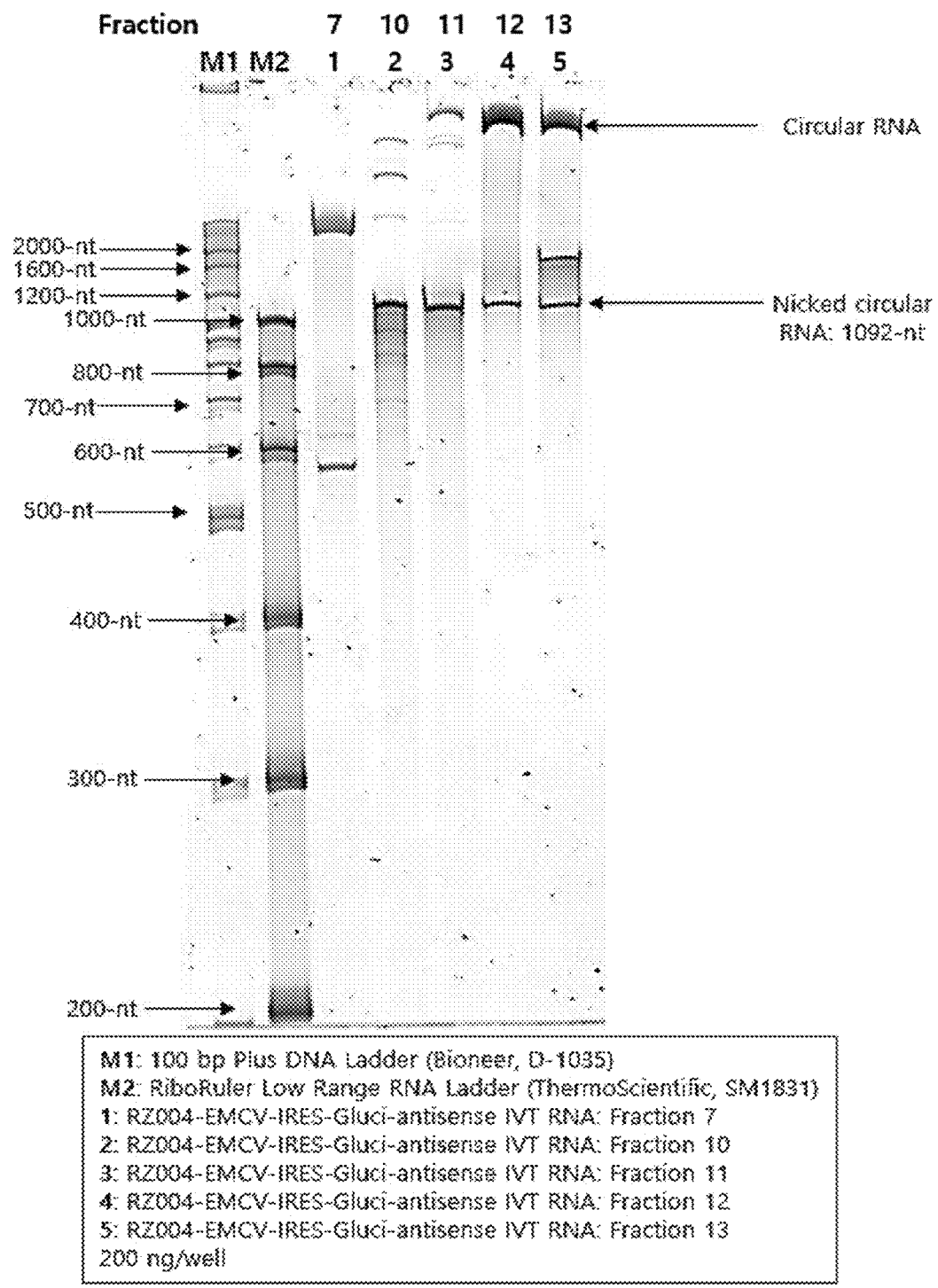

As a result, as can be seen in FIG. 8B, clean circular RNA was isolated and purified from fraction 12.

Example 5. AS (Antisense Sequence) Region Optimization

Figure 9:
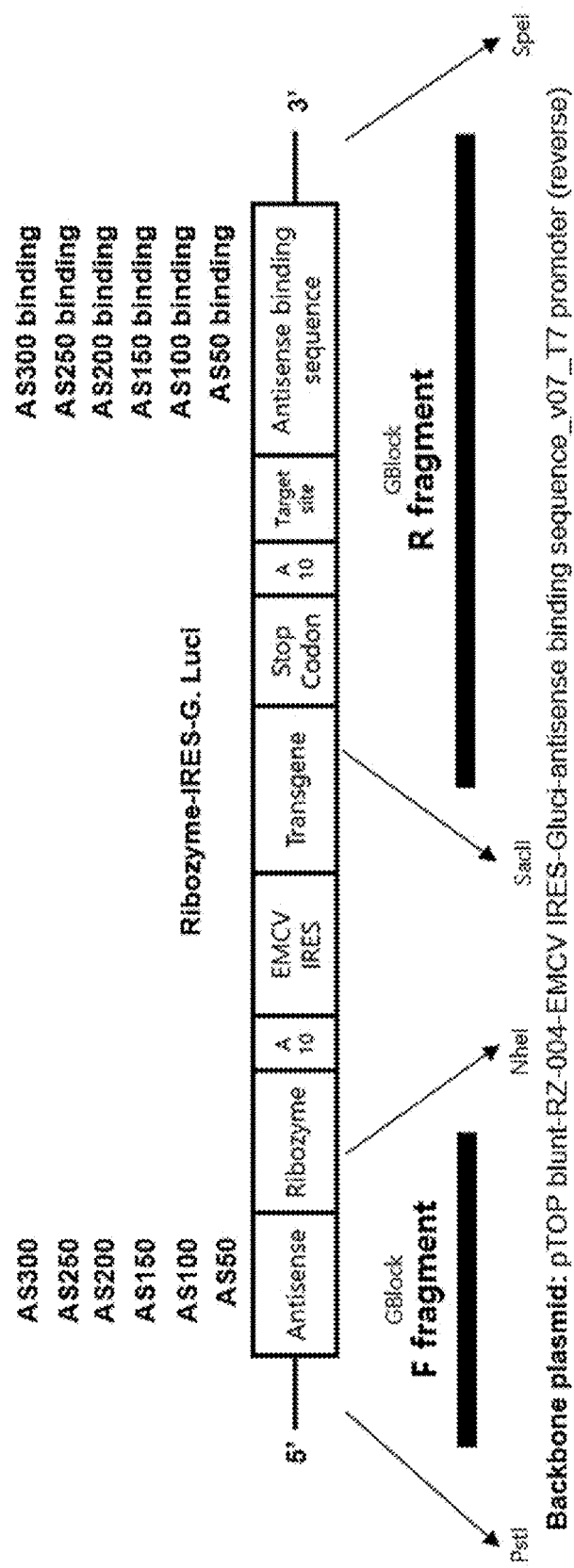
FIGS. 9 and 10 identify the effect of an AS region on STS reaction and circularization in a self-circularization RNA construct of an example embodiment of the present disclosure.

It was intended to identify the effect of the lengths of an antisense sequence (AS) region and a reverse-complementary antisense binding sequence (ABS) region on the immediate circularization reaction during an in vitro transcription process. Accordingly, a DNA template having different lengths of the AS region and ABS region of 50, 100, 150, 200, 250, or 300-nt was prepared (FIG. 9). A vector capable of expressing each RNA construct was produced in the same manner as in Example 1, and in vitro transcription was performed at 37° C. for 3 hours in the same manner as in Example 2. The degree of immediate STS reaction was compared and identified by relative band intensity by performing PAGE on 4% polyacrylamide-7 M urea gel (20×20 cm, 1 mm).

The nucleotide sequences of each AS region are shown in Table 1 below.

TABLE 1

| Sections | Nucleotide sequences (5' → 3') |
|---|---|
| AS50 | AAGTTAGGGCCTTCTGTGCCATTCATGGCTGTGGCCCTTGT GGCTGACCC (SEQ ID NO: 17) |
| AS100 | ACTCGAAGTGGCTGCGTACCACACCCGTCGCATTGGAGAAG GGCACGTAGAAGTTAGGGCCTTCTGTGCCATTCATGGCTGT GGCCCTTGTGGCTGACCC (SEQ ID NO: 18) |
| AS150 | GGCGGCCAGCATGGAGAACTGCCATGGCTCAGCCAGGTAGT ACTGTGGGTACTCGAAGTGGCTGCGTACCACACCCGTCGCA TTGGAGAAGGGCACGTAGAAGTTAGGGCCTTCTGTGCCATT CATGGCTGTGGCCCTTGTGGCTGACCC (SEQ ID NO: 19) |

TABLE 1-continued

| Sections | Nucleotide sequences (5' → 3') |
|---|---|
| AS200 | AGCGTGAGGAAGTTGATGGGGAAGCCCAGCACGATCAGCAG AAACATGTAGGCGGCCAGCATGGAGAACTGCCATGGCTCAG CCAGGTAGTACTGTGGGTACTCGAAGTGGCTGCGTACCACA CCCGTCGCATTGGAGAAGGGCACGTAGAAGTTAGGGCCTTC TGTGCCATTCATGGCTGTGGCCCTTGTGGCTGACCC (SEQ ID NO: 20) |
| AS250 | GGATGTAGTTGAGAGGCGTGCGCAGCTTCTTGTGCTGGACG GTGACGTAGAGCGTGAGGAAGTTGATGGGGAAGCCCAGCAC GATCAGCAGAAACATGTAGGCGGCCAGCATGGAGAACTGCC ATGGCTCAGCCAGGTAGTACTGTGGGTACTCGAAGTGGCTG CGTACCACACCCGTCGCATTGGAGAAGGGCACGTAGAAGTT AGGGCCTTCTGTGCCATTCATGGCTGTGGCCCTTGTGGCTG ACCC (SEQ ID NO: 21) |
| AS300 | GGTGAAGCCACCTAGGACCATGAAGAGGTCAGCCACGGCTA GGTTGAGCAGGATGTAGTTGAGAGGCGTGCGCAGCTTCTTG TGCTGGACGGTGACGTAGAGCGTGAGGAAGTTGATGGGGAA GCCCAGCACGATCAGCAGAAACATGTAGGCGGCCAGCATGG AGAACTGCCATGGCTCAGCCAGGTAGTACTGTGGGTACTCG AAGTGGCTGCGTACCACACCCGTCGCATTGGAGAAGGGCAC GTAGAAGTTAGGGCCTTCTGTGCCATTCATGGCTGTGGCCC TTGTGGCTGACCC (SEQ ID NO: 22) |

Figure 10:
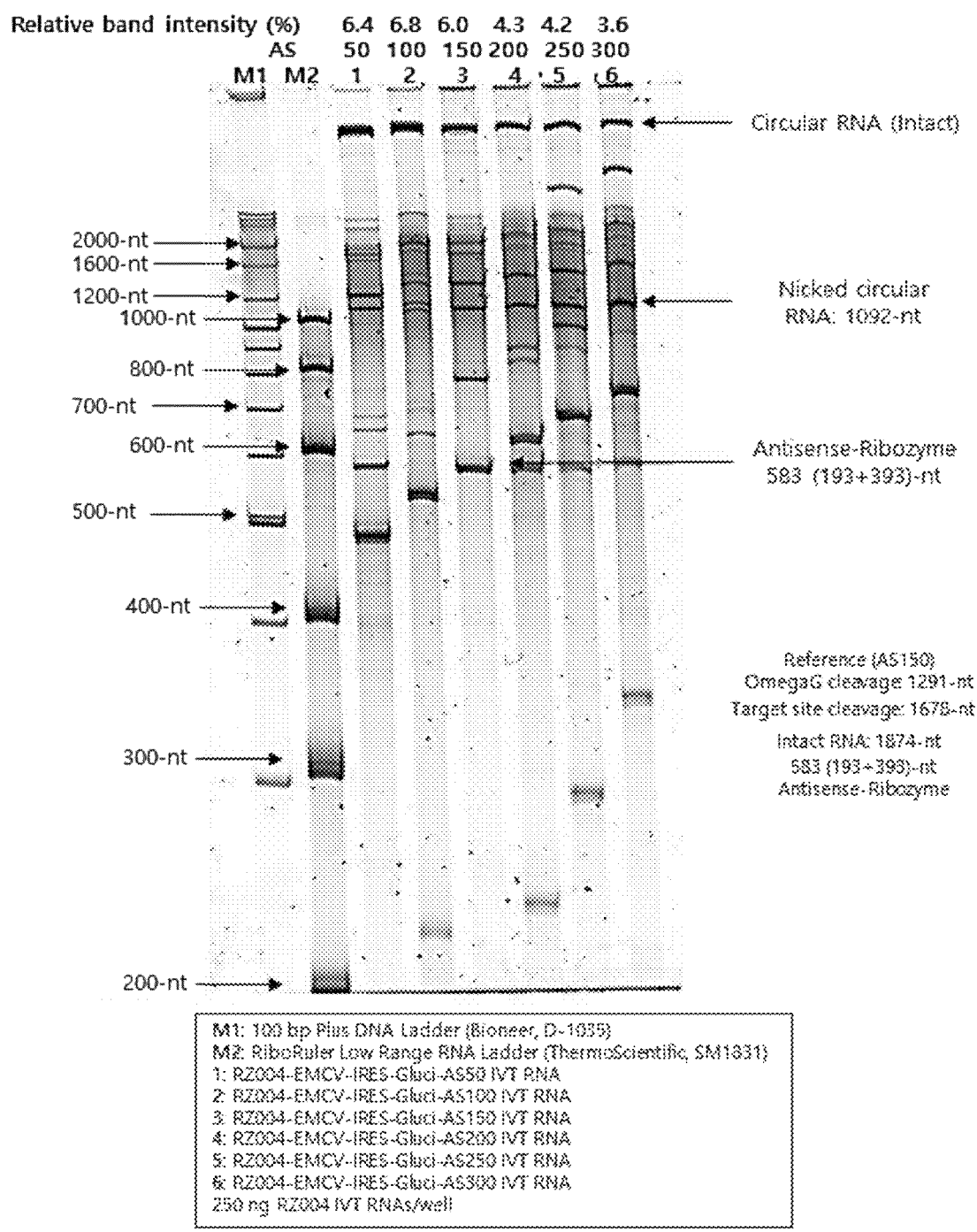

As a result, as can be seen in FIG. 10 and Table 2 below, in the case of AS50, AS100, and AS150, the self-circularization efficiency was relatively excellent compared to the length of AS200 or longer. On the other hand, for AS50 and AS100, total RNA produced after the in vitro transcription reaction was significantly less. Accordingly, it was found that AS150 was the most optimal length for self-circularization RNA construct expression and circular RNA production.

TABLE 2

| | AS series | | | | | |
|---|---|---|---|---|---|---|
| | AS50 | AS100 | AS150 | AS200 | AS250 | AS300 |
| A: Amount of Total RNA produced (μg) | 69.5 ± 1.77 | 9.15 ± 0.46 | 176.5 ± 3.89 | 140 ± 3.54 | 133 ± 2.83 | 141 ± 5.66 |
| B: Relative band intensity of circular RNA (%) | 6.35 ± 0.25 | 6.75 ± 0.04 | 5.95 ± 0.18 | 4.30 ± 0.07 | 4.20 ± 0.07 | 3.60 ± 0.14 |
| Relative factor (A * B) | 441 | 62 | 1050 | 602 | 559 | 508 |

Example 6. Spacer Region Optimization

Figure 11:
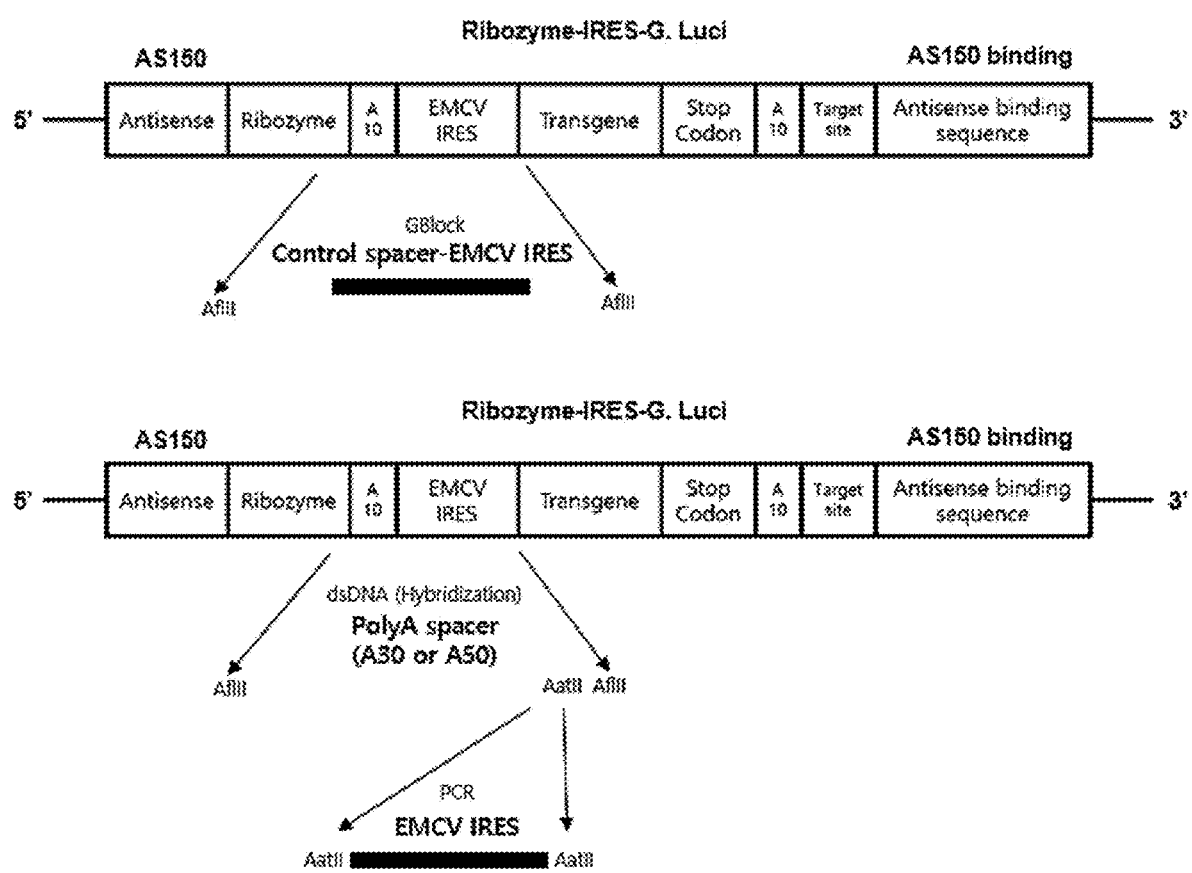
FIGS. 11 and 12 identify the effect of a spacer region on STS reaction and circularization in a self-circularization RNA construct of an example embodiment of the present disclosure.

Subsequently, in order to identify the effect of the length or type of the spacer region on the immediate circularization reaction during an in vitro transcription process, a DNA template including spacer regions of different lengths and nucleotide sequences was produced (FIG. 11). A vector capable of expressing each RNA construct was produced in the same manner as in Example 1, and in vitro transcription was performed at 37° C. for 3 hours in the same manner as in Example 2. The degree of immediate STS reaction was compared and identified by relative band intensity by performing PAGE on 4% polyacrylamide-7 M urea gel (20×20 cm, 1 mm). The nucleotide sequences of each spacer region are shown in Table 3 below. In this experiment, the spacers of A10, A30, and A50 were used by adding a restriction recognition site at the 3' end for IRES insertion immediately after the spacer region. In this experiment, the AatII site (GACGTC) (SEQ ID NO: 48) was added to the 3' end of the spacer and used.

TABLE 3

| Sections | Nucleotide sequences (5' → 3') |
|---|---|
| A10 | AAAAAAAAAA (SEQ ID NO: 23) |
| A30 | AAAAAAAAAAAAAAAAAAAAAAAAAAAAAA (SEQ ID NO: 24) |
| A50 | AAAAAAAAAAAAAAAAAAAAAAAAAAAAAAAAAAAAAAAAAAAAAAAAAA (SEQ ID NO: 25) |
| Control spacer 1 | GGTAGTGGTGCTACTAACTTCAGCCTGCTGAAGCA (SEQ ID NO: 26) |
| Control spacer 2 | GGTAGTAAACTACTAACTACAACCTGCTGAAGCA (SEQ ID NO: 27) |

Figure 12:
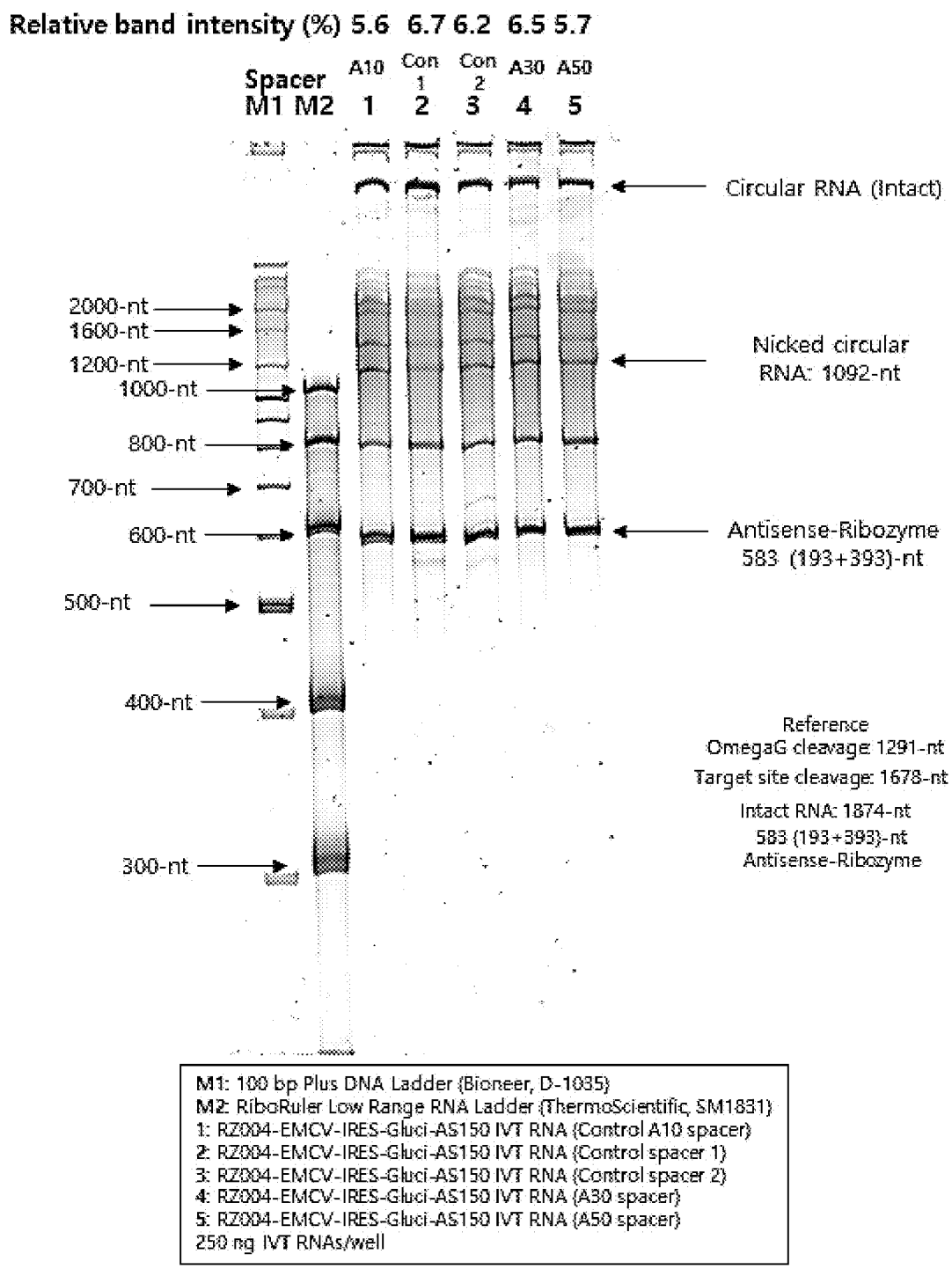

As a result, as can be seen in FIG. 12 and Table 4 below, despite the difference in the length and sequence of the spacer, there was no significant difference in the immediate circularization efficiency in the in vitro transcription process, but it was found that A30 operated as the most optimal spacer for self-circularization RNA construct expression and circular RNA production.

TABLE 4

| AS150 Spacer version | A10 | Control spacer 1 | Control spacer 1 | A30 | A50 |
|---|---|---|---|---|---|
| A: Amount of Total RNA produced (μg) | 199.5 ± 9.19 | 199.5 ± 6.36 | 187 ± 5.66 | 190 ± 8.49 | 192.5 ± 0.71 |
| B: Relative band intensity of circular RNA (%) | 5.55 ± 0.35 | 6.7 ± 0.14 | 6.15 ± 0.07 | 6.5 ± 1.27 | 5.7 ± 0.85 |
| Relative factor (A * B) | 1106 ± 19 | 1311 ± 70 | 1150 ± 21 | 1240 ± 297 | 1097 ± 160 |

Example 7. Optimization of Self-Circularization RNA Construct

7-1. AS Region, and P1 Helix and P10 Helix Regions

The self-circularization RNA construct designed in Example 1 includes an AS region, and P1 helix and P10 helix regions. Hereinafter, in order to identify the effect of each configuration on the immediate circularization reaction during the in vitro transcription process, as diagrammed in FIG. 13, a DNA template including only the P1 helix region, only the P1 and P10 helix regions, or both the P1 and P10 helixes and the AS region was prepared. A vector capable of expressing each RNA construct was produced in the same manner as in Example 1, and in vitro transcription was performed at 37 C for 3 hours in the same manner as in Example 2. The degree of immediate STS reaction was compared and identified by relative band intensity by performing PAGE on 4% polyacrylamide-7 M urea gel (20×20 cm, 1 mm).

The nucleotide sequences of the T7 DNA template including only the P1 helix region are shown in FIG. 14.

Figure 15:
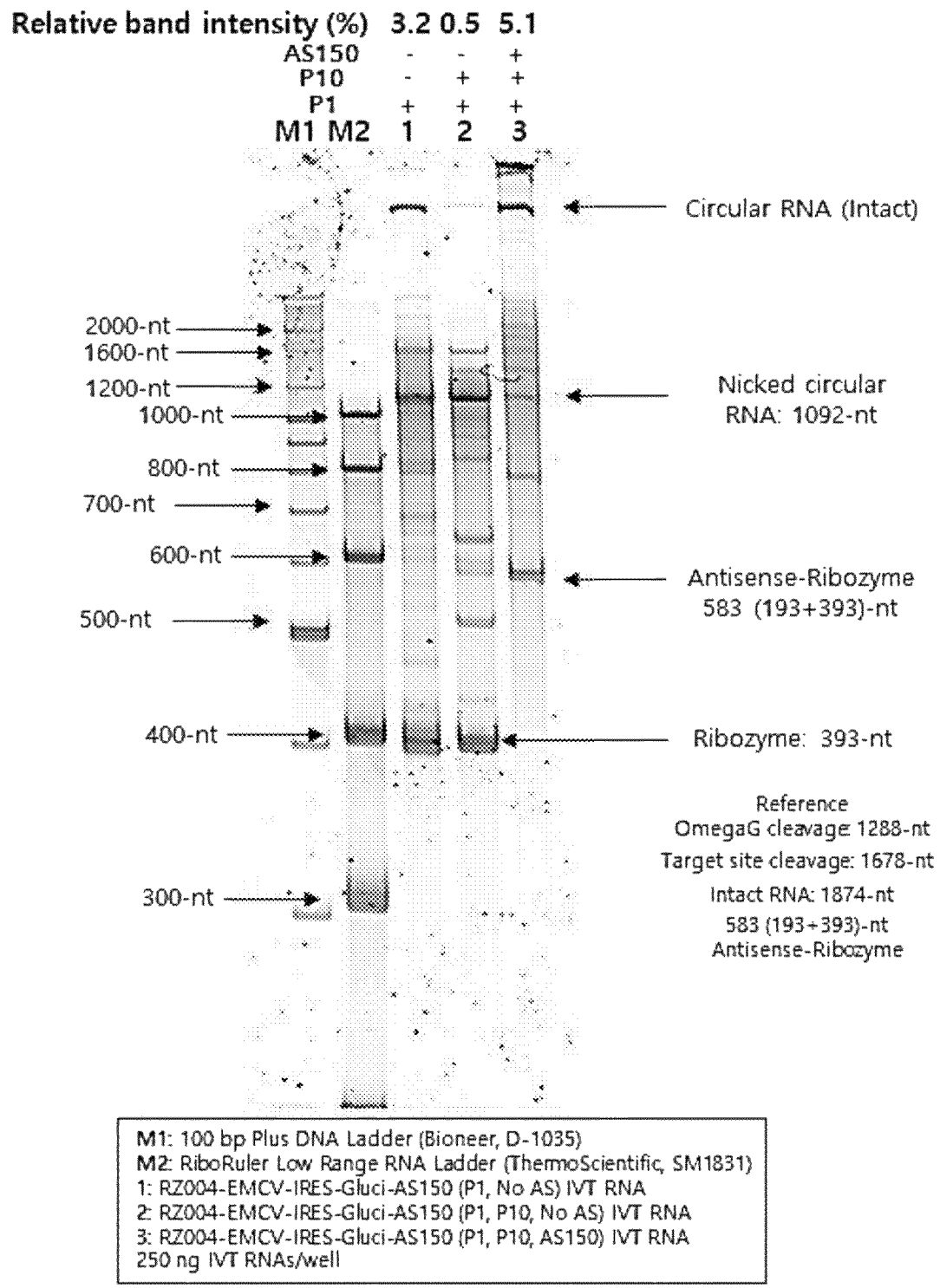
FIG. 15 shows an electrophoresis result of a sample obtained after in vitro transcription of each self-circularization RNA expression vector of FIG. 13.

As a result, as can be seen in FIG. 15 and Table 5 below, there was no significant difference in the total RNA transcribed and generated in each vector in vitro, but it was found that the circular RNA production amount was high in the order of including both the P1 and P10 helix and the AS regions, including only the P1 helix region, and including only the P1 and P10 regions.

TABLE 5

| AS150 | P1 (No AS) | P1&P10 (No AS) | P1&P10 (AS150) |
|---|---|---|---|
| A: Amount of Total RNA produced (µg) | 200 | 196 | 182 |
| B: Relative band intensity of circular RNA(%) | 3.2 | 0.5 | 5.1 |
| Relative factor (A * B) | 640 | 98 | 928 |

7-2. Circularization Verification of Self-Circularization RNA Construct that does not Include P10 and AS Regions From the results of Example 7-1, it can be understood that sufficient circRNAs could be produced without an additional circularization stage in the in vitro transcription process from a DNA template (P1 construct) that does not include P10 and AS regions. In order to verify this, the product after the STS reaction of Example 7-1 was treated with RNase R to remove linear RNA, PAGE was performed in the same manner as in the previous experiment, and RT-PCR and sequencing were performed in the same manner as in Example 2-2.

Figure 16A:
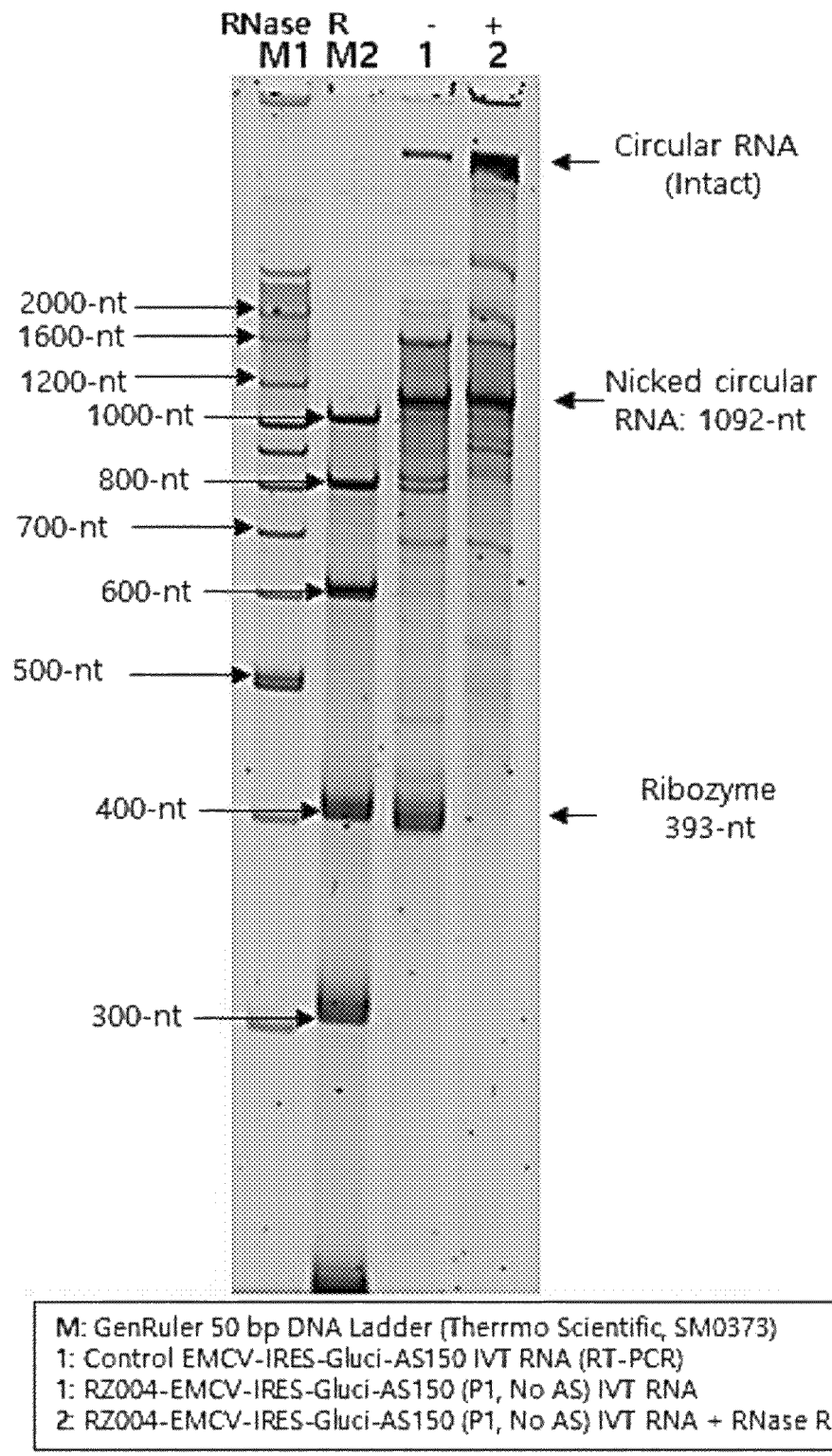
FIGS. 16A and 16B show the results identified through electrophoresis that a self-circularization RNA construct is formed into a circRNA after in vitro transcription in a self-circularization RNA expression vector including only a P1 region without P10 and AS regions.
Figure 16B:
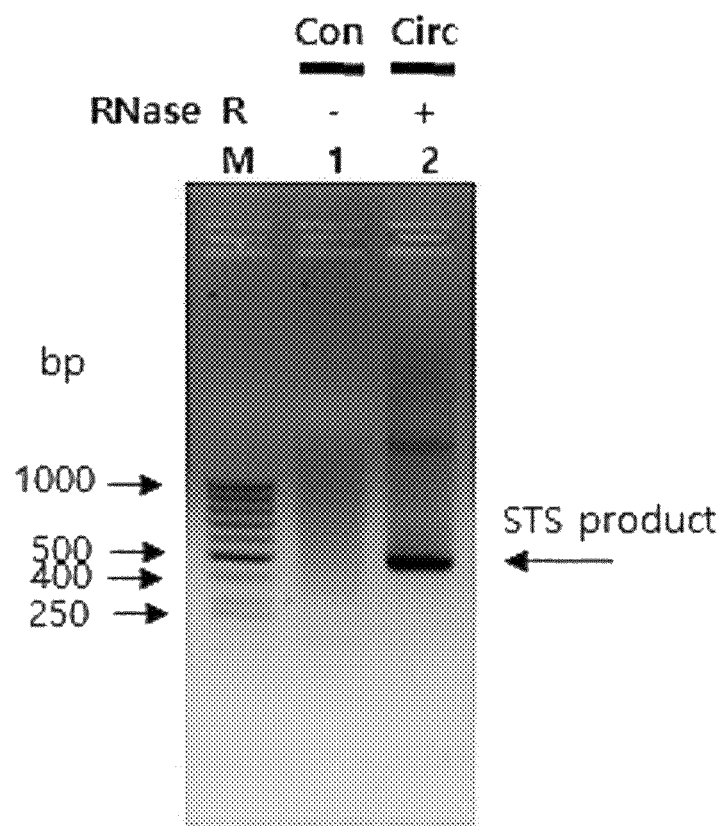

As a result, as can be seen in FIGS. 16A and 16B, even when self-circularization was performed using the P1 construct, when RNase R was treated, an RNA band that was not easily cut by RNase R and enriched was observed. As a result of performing RT-PCR and sequencing of the STS reaction product in the band, it was identified that it was a circRNA.

Example 8. Optimization of P1 Helix Region

From the results of Example 7, it was identified that the self-circularization construct without P10, AS, and ABS could also sufficiently make a circRNA. Accordingly, it was intended to verify assuming that a circular RNA would be generated only when the Internal Guide Sequence (IGS) present at the 5' end and the nucleotide sequence of the target site present at the 3' end configuring the P1 helix are complementarily bound to each other (U and G are wobble base pairs).

Since the IGS region is G (SEQ ID NO: 1) and the nucleotide sequence of the target site is N'N'N'N'N'U (SEQ ID NO: 2), when only one U nucleotide is added to the GOI, the final product circRNA consists only of one additional U base and the GOI region (FIGS. 1A and 1B). In addition, when the 3' end of the GOI ends with a U base, by designing the nucleotide sequence of the IGS region to be reverse-complementary to the GOI, the circRNA finally generated may be prepared to consist only of the GOI region (FIGS. 20A and 20B).

Figure 17:
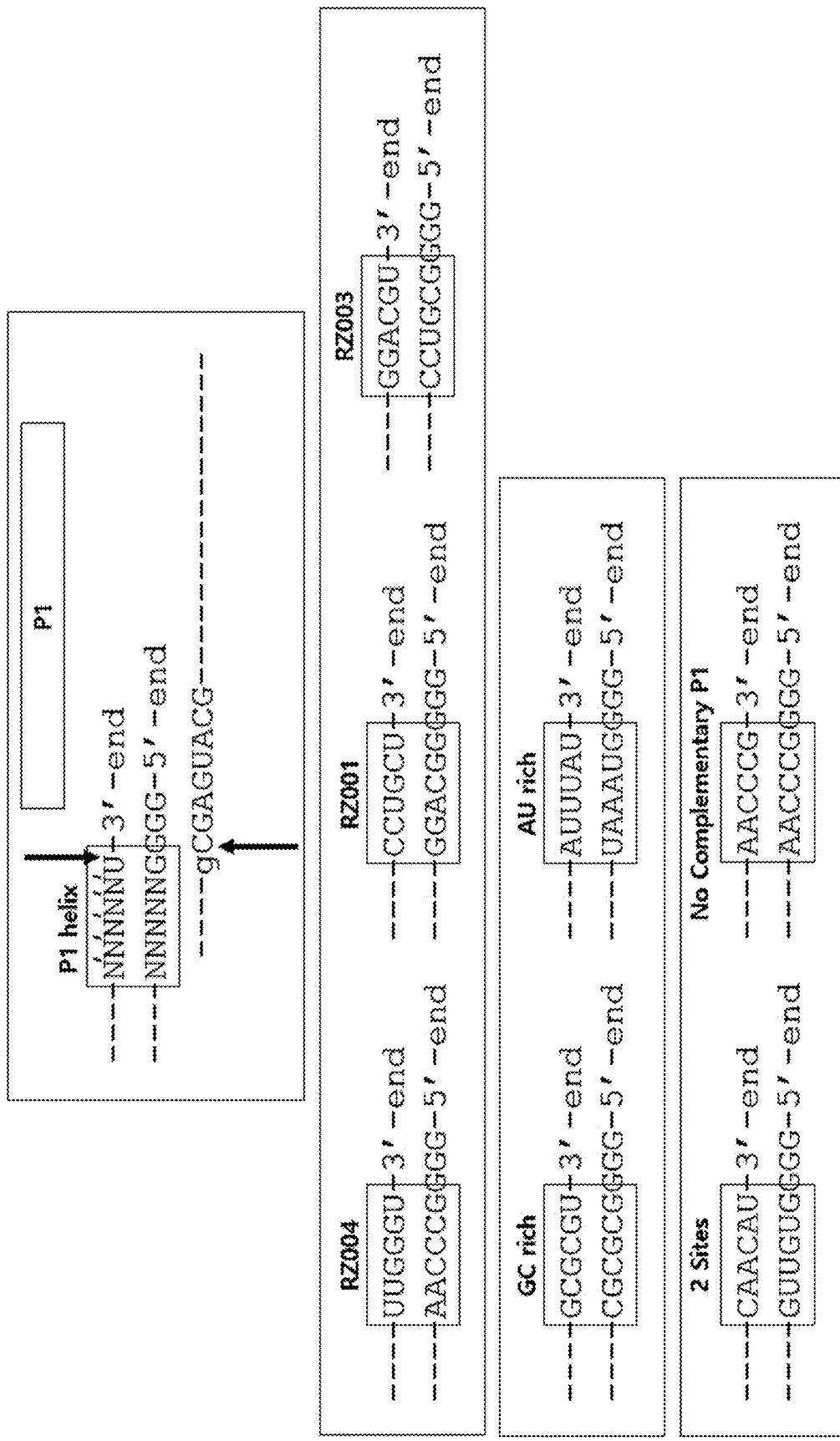
FIGS. 17 to 19 identify the effect of a nucleotide sequence of a P1 region on STS reaction and circularization in a self-circularization RNA construct of an example embodiment of the present disclosure. Specifically.

As shown in FIG. 17, various sequences of IGS and target site were designed, a vector was produced by the method of Example 1, and then the in vitro transcription of Example 2-1 was performed.

Figure 18:
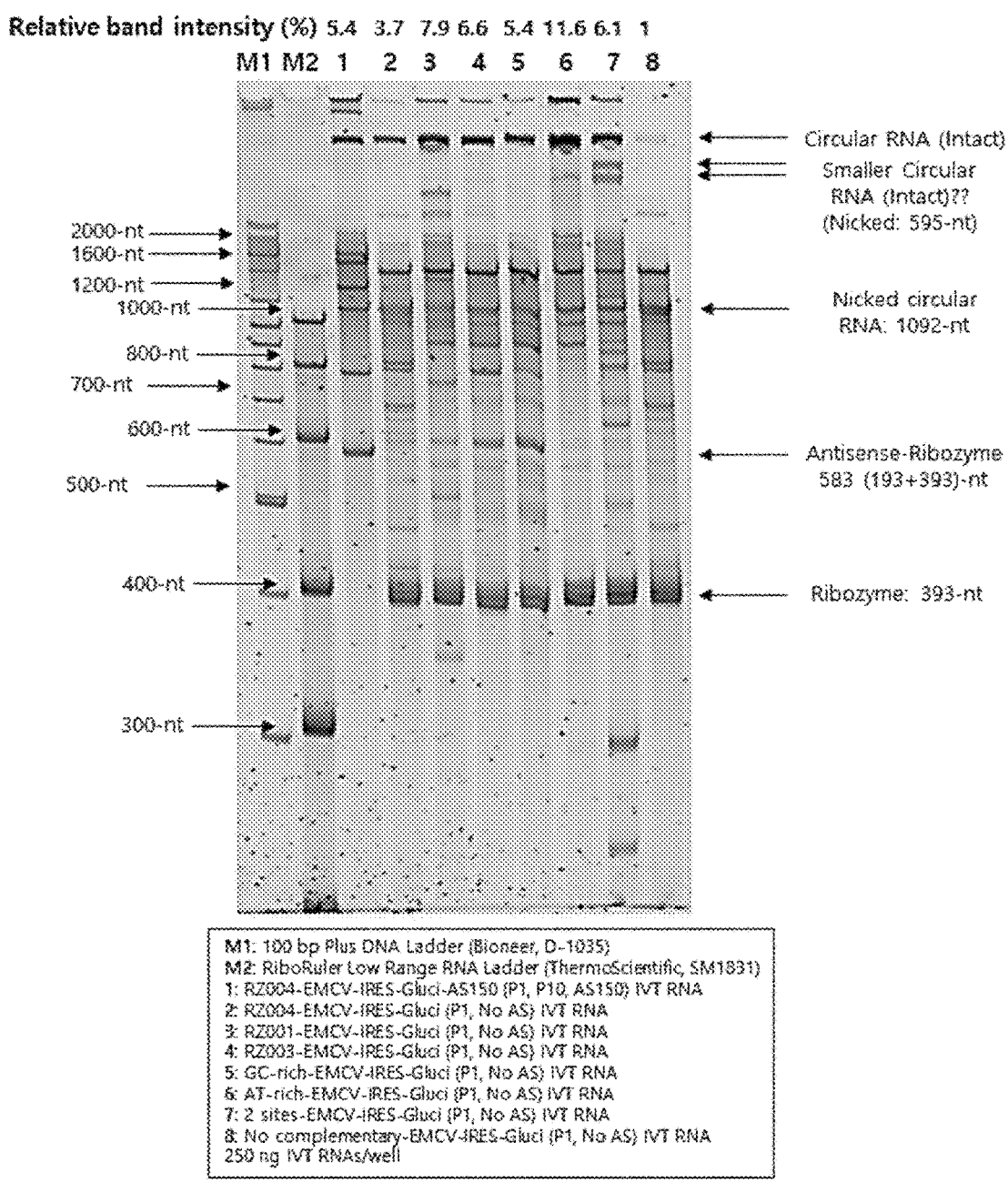
Figure 19:
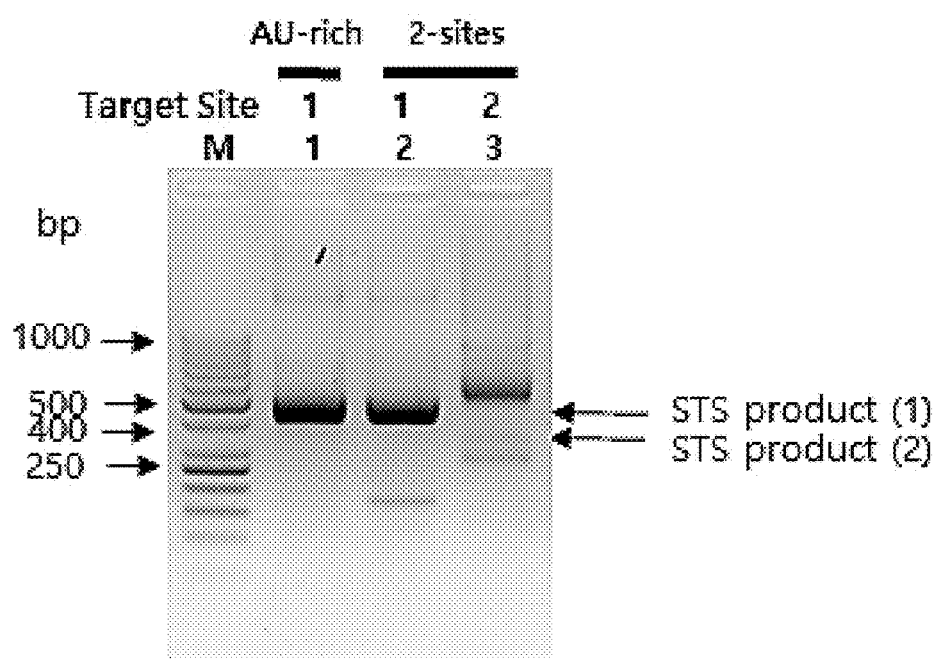

As a result, as can be seen in FIGS. 18-19 and Table 6 below, when both ends have complementary sequences, it was possible to identify an increase in the circRNA generated through the immediate STS reaction after in vitro transcription, and it was found that the vector including the no-complement IGS region generated a very low level of a circRNA. From the above, it was found that both the IGS and the target site could efficiently induce a self-circularization reaction when they were complementary to each other.

TABLE 6

| P1 variants (No AS) | AS150 (P1&P10) | RZ004 | RZ001 | RZ003 | GC-rich | AU-rich | 2 sites | No complement |
|---|---|---|---|---|---|---|---|---|
| Relative band intensity of circular RNA (%) | 5.4 | 3.7 | 7.9 | 6.6 | 5.4 | 11.6 | 6.1 | 1 |

As described above, although the example embodiments have been described with reference to the limited drawings, those skilled in the pertinent technical field may apply various technical modifications and variations based on the above. For example, proper results may be achieved although the described techniques are performed in an order different from the described method, and/or the described components, such as a system, structure, device, circuit, etc., are coupled or combined in a form different from the described method or replaced or substituted by other components or equivalents.

Accordingly, other implementations, other example embodiments, and the equivalents of the claims also belong to the scope of the claims below.

The present disclosure may be used for the production of circRNAs for protein expression in vitro, in cells, and in vivo, and may be used to produce miRNA, anti-miRNA, shRNA, aptamer, mRNA vaccine, mRNA therapeutic agent, antibody, vaccine adjuvant, functional RNA for gene/RNA/base editing, and functional RNA of CAR-T mRNA into a circRNA.

The foregoing description of illustrative embodiments of the disclosure have been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with in various modifications as suited to the particular use contemplated. It is intended that the scope of the disclosure be defined by the claims appended hereto and their equivalents.

The invention claimed is:

1. A self-circularization RNA construct comprising, from the 5'-terminus to the 3'-terminus:
   a) an internal guide sequence (IGS) region comprising guanine (G) at the 5'-end;
   b) a ribozyme region wherein the ribozyme region is a Group I intron ribozyme;
   c) a gene of interest (GOI) region; and
   d) a fragment containing target splice site comprising uracil (U) at the 3'-end, wherein the 5'-end G of the IGS region and the 3'-end U of the target splice site-containing fragment form a G : U wobble base pair, wherein the a) IGS region comprises a sequence of 2 to 10 contiguous nucleotides, which is reverse complementary to a 3'-end portion nucleotide sequence of the d) target splice site-containing fragment, and wherein the self-circularization RNA construct allows production of a circular RNA comprising the c) gene of interest region and the d) target splice site-containing fragment, but not the b) ribozyme region and the a) IGS region.

2. The self-circularization RNA construct of claim 1, wherein the b) ribozyme region does not contain an exon fragment.

3. The self-circularization RNA construct of claim 1, wherein a part or entirety of the 3'-end portion nucleotide sequence of the d) fragment containing target splice site constitutes a 3'-end portion sequence of the c) GOI region.

4. The self-circularization RNA construct of claim 1, wherein the b) ribozyme region comprises the nucleotide sequence of SEQ ID NO: 6.

5. The self-circularization RNA construct of claim 1, wherein the self-circularization RNA construct further comprises a 2-nt to 20-nt contiguous nucleotide sequence extended from the 5'-end guanine (G) of the a) IGS region, said contiguous nucleotide sequence is reverse complementary to a sequence linked to the 3'-end of the b) ribozyme region to form a P10 helix structure, and wherein the circular RNA does not include the 2-nt to 20-nt contiguous nucleotide sequence extended from the 5'-end guanine (G) of the a) IGS region.

6. The self-circularization RNA construct of claim 1, wherein the self-circularization RNA construct further comprises a 2-nt to 20-nt contiguous nucleotide sequence extended from the 5':-end guanine (G) of the a) IGS region, said contiguous nucleotide sequence is not reverse complementary to a sequence linked to the 3'-end of the b) ribozyme region and is not capable of forming a P10 helix structure, and wherein the circular RNA does not include the 2-nt to 20-nt contiguous nucleotide sequence extended from the 5'-end guanine (G) of the a) IGS region.

7. The self-circularization RNA construct of claim 5, wherein the self-circularization RNA construct further comprises a 2-nt to 20-nt contiguous nucleotide sequence extended from the 3':-end uracil (U) of the d) target splice site-containing fragment, said contiguous nucleotide sequence extended from the 3'-end uracil (U) is capable of forming a P1 helix structure with the 2-nt to 20-nt contiguous nucleotide sequence extended from the 5'-end guanine (G) of the a) IGS region.

8. The self-circularization RNA construct of claim 6, wherein the self-circularization RNA construct further comprises a 2-nt to 20-nt contiguous nucleotide sequence extended from the 3'-end uracil (U) of the d) target splice site-containing fragment, said contiguous nucleotide sequence extended from the 3'-end uracil (U) is capable of forming a P1 helix structure with the 2-nt to 20-nt contiguous nucleotide sequence extended from the 5'-end guanine (G) of the a) IGS region.

9. The self-circularization RNA construct of claim 1, wherein the self-circularization RNA construct further comprises an antisense sequence (AS) region upstream of the a) IGS region and an antisense binding sequence (ABS) region downstream of the d) target splice site, said ABS region being capable of complementary binding to the AS region.

10. The self-circularization RNA construct of claim 9, wherein a length of the AS region is 10-nt to 400-nt.

11. The self-circularization RNA construct of claim 5, wherein the self-circularization RNA construct further comprises an antisense sequence (AS) region upstream of the a) IGS region and an antisense binding sequence (ABS) region downstream of the d) target splice site-containing fragment capable of complementary binding to the AS region.

12. The self-circularization RNA construct of claim 11, wherein a length of the AS region is 10-nt to 400-nt.

13. The self-circularization RNA construct of claim 6, wherein the self-circularization RNA construct further comprises an antisense sequence (AS) region upstream of the a) IGS region and an antisense binding sequence (ABS) region downstream of the d) target splice site-containing fragment capable of complementary binding to the AS region.

14. The self-circularization RNA construct of claim 13, wherein a length of the AS region is 10-nt to 400-nt.

15. The self-circularization RNA construct of claim 7, wherein the self-circularization RNA construct further comprises an antisense sequence (AS) region upstream of the a) IGS region and an antisense binding sequence (ABS) region downstream of the d) target splice site-containing fragment capable of complementary binding to the AS region.

16. The self-circularization RNA construct of claim 15, wherein a length of the AS region is 10-nt to 400-nt.

17. The self-circularization RNA construct of claim 1, wherein the c) gene of interest (GOI) sequence region comprises an internal ribosome entry site (IRES), a spacer sequence, or a combination thereof.

18. The self-circularization RNA construct of claim 1, wherein the c) gene of interest (GOI) sequence region is a coding sequence, a non-coding sequence, or a combination thereof.

19. A vector comprising a sequence encoding the self-circularization RNA construct of claim 1, wherein the self-circularization RNA construct comprising, from the 5'-terminus to the 3'-terminus:
a) an internal guide sequence (IGS) region comprising guanine (G) at the 5'-end;
b) a ribozyme region wherein the ribozyme region is a Group I intron ribozyme;
c) a gene of interest (GOI) region; and
d) a fragment containing target splice site comprising uracil (U) at the 3'-end, wherein the 5'-end G of the IGS region and the 3'-end U of the target splice site-containing fragment form a G : U wobble base pair, and wherein the a) IGS region comprises a sequence of 2 to 10 contiguous nucleotides, which is reverse complementary to a 3'-end portion nucleotide sequence of the d) target splice site region.

20. The vector of claim 19, wherein the vector comprises a promoter operably linked to the sequence encoding the self-circularization RNA construct.

21. A circular RNA produced by the vector of claim 19, wherein the circular RNA comprises the c) gene of interest sequence (GOI) region and the 3'-end uracil (U) of the d) target splice site or wherein the circular RNA comprises the gene of interest (GOI) sequence region that comprises the target splice site including the d) 3'-end uracil (U), and wherein the circular RNA does not contain the b) ribozyme region and the a) IGS region.

22. A cell or cell population comprising the circular RNA of claim 21.

23. A method of producing a circular RNA in a cell population or making a cell population comprising the circular RNA, said method comprising contacting cells of the cell population with a composition comprising:
a) (1) the self-circularization RNA construct of claims 1 and (2) a delivery vehicle for delivering the circular RNA to the cells, said delivery vehicle comprising a nanocarrier selected from the group consisting of a lipid, a polymer and a lipo-polymeric hybrid,
b) (1) a vector comprising the self-circularization RNA construct of claims 1, and (2) a delivery vehicle for delivering the circular RNA to the cells, said delivery vehicle comprising a nanocarrier selected from the group consisting of a lipid, a polymer and a lipo-polymeric hybrid; or
c) (1) the circular RNA produced by the vector of b)(1), and (2) a delivery vehicle for delivering the circular RNA to the cells, said delivery vehicle comprising a nanocarrier selected from the group consisting of a lipid, a polymer and a lipo-polymeric hybrid.

24. A composition comprising:
a) an effective amount of the self-circularization RNA construct of claim 1, a vector comprising the self-circularization RNA construct of claim 1, or a circular RNA produced by the self-circularization RNA construct or the vector comprising the self-circularization RNA construct, and
b) a delivery vehicle for delivering the circular RNA to a cell, said delivery vehicle comprising a nanocarrier selected from the group consisting of a lipid, a polymer and a lipo-polymeric hybrid.

25. The self-circularization RNA construct of claim 8, wherein the self-circularization RNA construct further comprises an antisense sequence (AS) region upstream of the a) IGS region and an antisense binding sequence (ABS) region downstream of the d) target splice site, said ABS region being capable of complementary binding to the AS region.

26. The self-circularization RNA construct of claim 25, wherein a length of the AS region is 10-nt to 400-nt.

27. The self-circularization RNA construct of claim 17, wherein the spacer is 7 nt-100 nt.

* * * * *